United States Patent
Shu et al.

[11] Patent Number: 6,139,575
[45] Date of Patent: Oct. 31, 2000

[54] HYBRID MECHANICAL HEART VALVE PROSTHESIS

[75] Inventors: Mark C. S. Shu, Mission Viego; Hong S. Shim, Santa Ana; Jeffrey M. Gross, Rancho Santa Margaarita, all of Calif.

[73] Assignee: Medtronic, Inc., Minneapolis, Minn.

[21] Appl. No.: 09/286,095

[22] Filed: Apr. 2, 1999

[51] Int. Cl.$^7$ .................................................. A61F 2/06
[52] U.S. Cl. ............................................ 623/2.12; 623/2.2
[58] Field of Search ....................... 623/2.1, 2.12, 623/2.13, 2.14, 2.15, 2.16, 2.17, 2.19, 2.2

[56] References Cited

U.S. PATENT DOCUMENTS

| | | |
|---|---|---|
| 3,396,409 | 8/1968 | Melrose . |
| 3,722,004 | 3/1973 | Cromie . |
| 3,911,502 | 10/1975 | Boretos ........................................ 3/1.5 |
| 4,204,283 | 5/1980 | Bellhouse et al. ........................ 623/2.2 |
| 4,222,126 | 9/1980 | Boretos ........................................ 3/1.5 |
| 4,276,658 | 7/1981 | Hanson et al. ............................. 3/13.5 |
| 4,364,127 | 12/1982 | Pierce et al. ................................ 3/1.5 |
| 4,473,423 | 9/1984 | Kolff ...................................... 156/245 |
| 4,510,628 | 4/1985 | Kolff ........................................... 3/1.5 |
| 4,556,996 | 12/1985 | Wallace ...................................... 623/2 |
| 4,643,732 | 2/1987 | Pietsch et al. ............................ 623/2.2 |
| 4,731,075 | 3/1988 | Gallo et al. .................................. 623/2 |
| 5,133,845 | 7/1992 | Vallana .................................. 204/192.5 |
| 5,178,632 | 1/1993 | Hanson ..................................... 632/2 |
| 5,370,684 | 12/1994 | Vallana et al. .............................. 623/1 |
| 5,447,724 | 9/1995 | Helmus et al. ......................... 424/426 |
| 5,500,016 | 3/1996 | Fisher ......................................... 623/2 |
| 5,562,729 | 10/1996 | Purdy et al. ................................. 623/2 |
| 5,569,463 | 10/1996 | Helmus et al. ......................... 424/426 |

FOREIGN PATENT DOCUMENTS

WO 99/04731  2/1999  WIPO ............................... A61F 2/24

OTHER PUBLICATIONS

The Return of Elastomer Valves (The Society of Thoracic Surgeons 1989;48:S98–9) William J. Kolff et al.

*Primary Examiner*—David J Isabella
*Attorney, Agent, or Firm*—Harold R. Patton

[57] ABSTRACT

A prosthetic mechanical heart valve, and in particular, a bi-leaflet and/or a trileaflet mechanical valve formed with rigid frame and hinge elements for providing a stable reliable hinge mechanism with flexible leaflets formed of a thin elastomeric material adhering to and extending from the valve frame to form leaflet occluding sections bounded by outer peripheral edges for softening the opening and closing action of the valve leaflets. In one embodiment, the valve leaflet is formed of a rigid pyrolytic carbon frame supporting hinge elements and defining a leaflet pivot axis and a flexible leaflet body attached to the frame and defining a leaflet abutting section extending from one side of the valve frame and an occluding section extending from the other side of the valve frame to an arcuate leaflet seat. In the closing phase of operation, the abutting sections of the leaflet bodies contact one another in an abutting contact band, and the arcuate leaflet seats bear against arcuate seat regions of the valve body The seat regions of the valve body may also be coated with an elastomeric material.

23 Claims, 11 Drawing Sheets

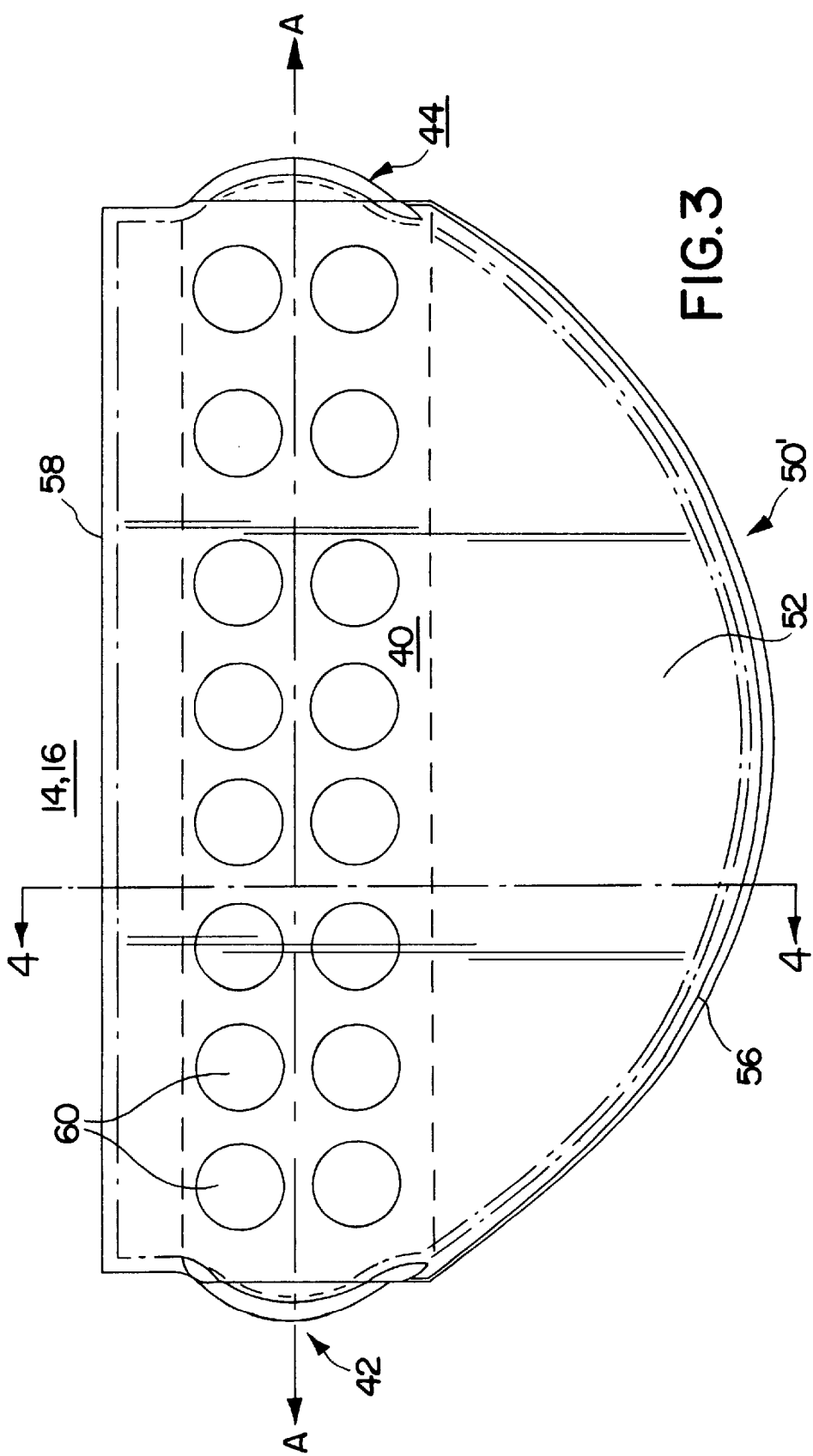

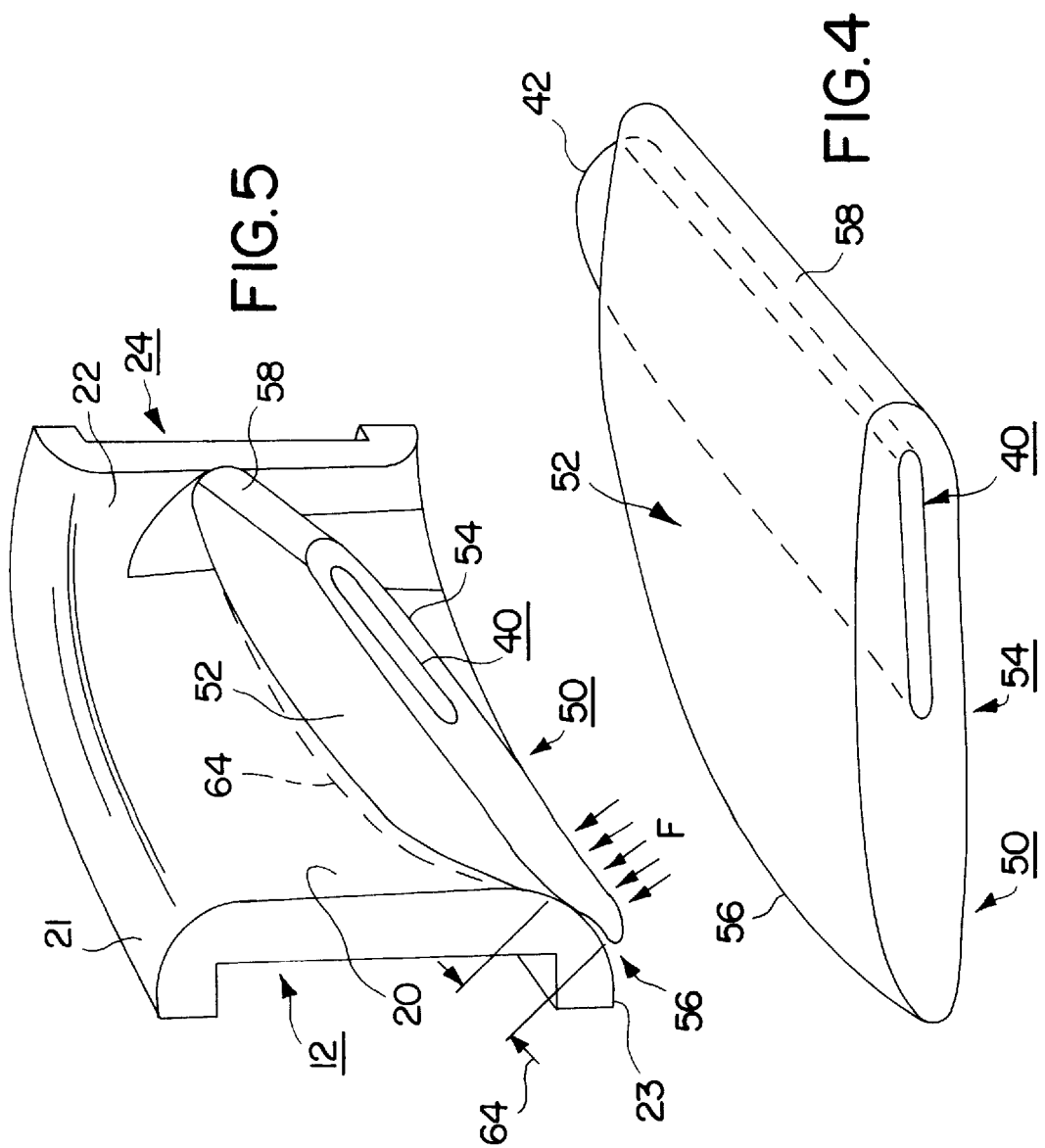

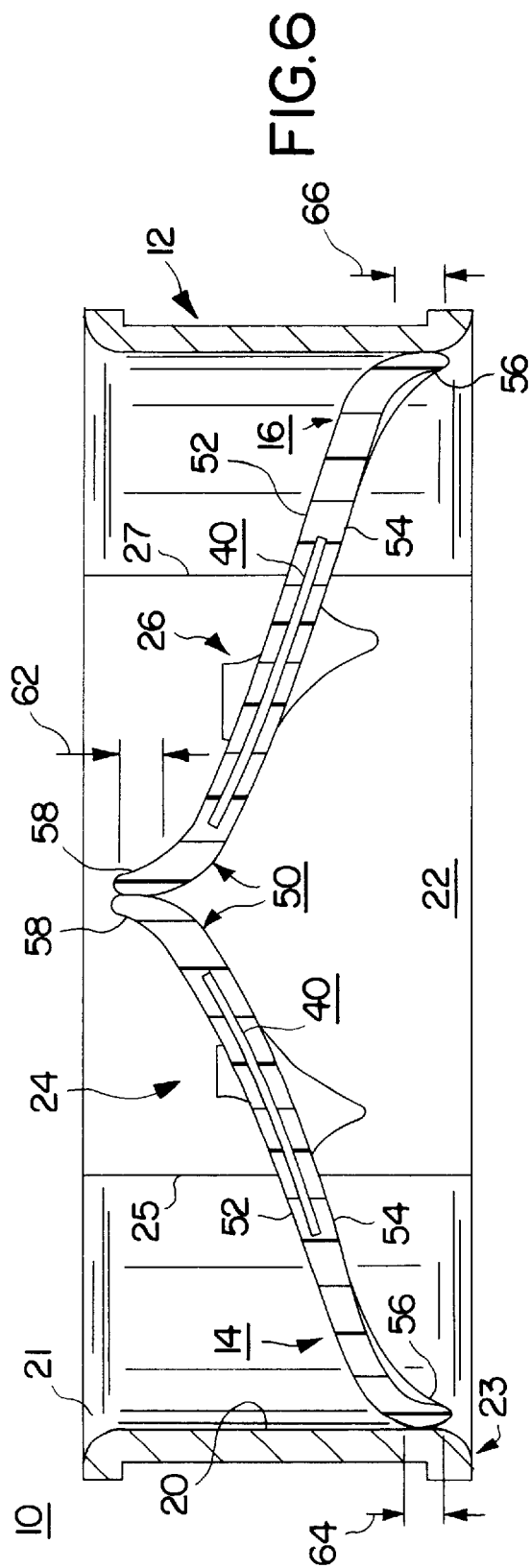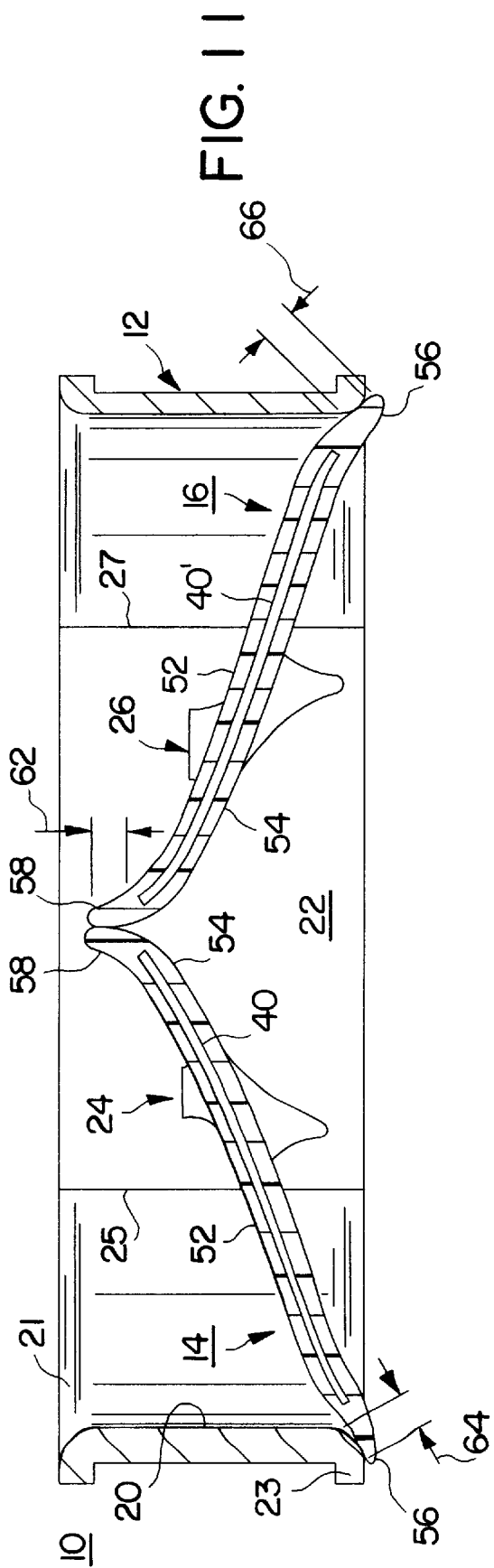

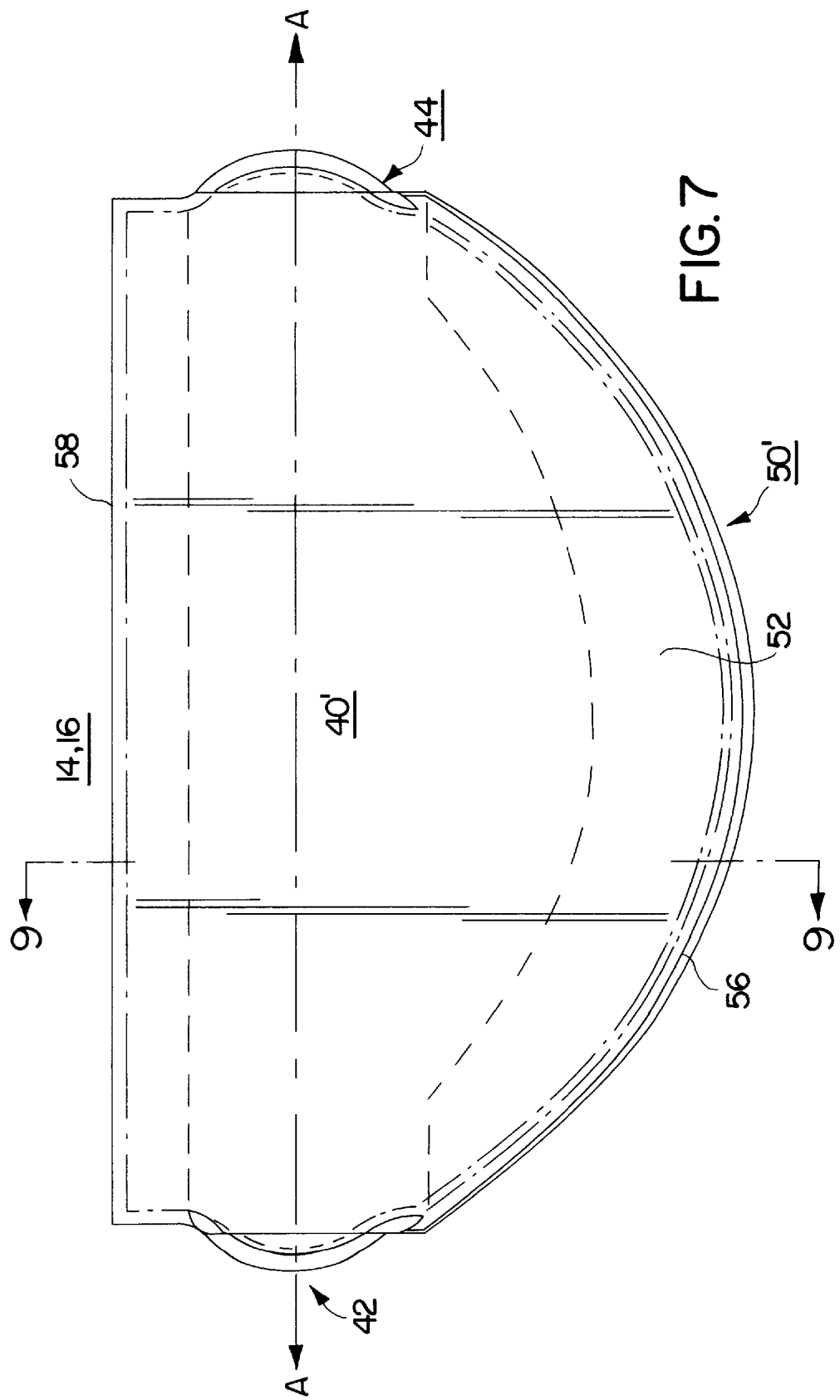

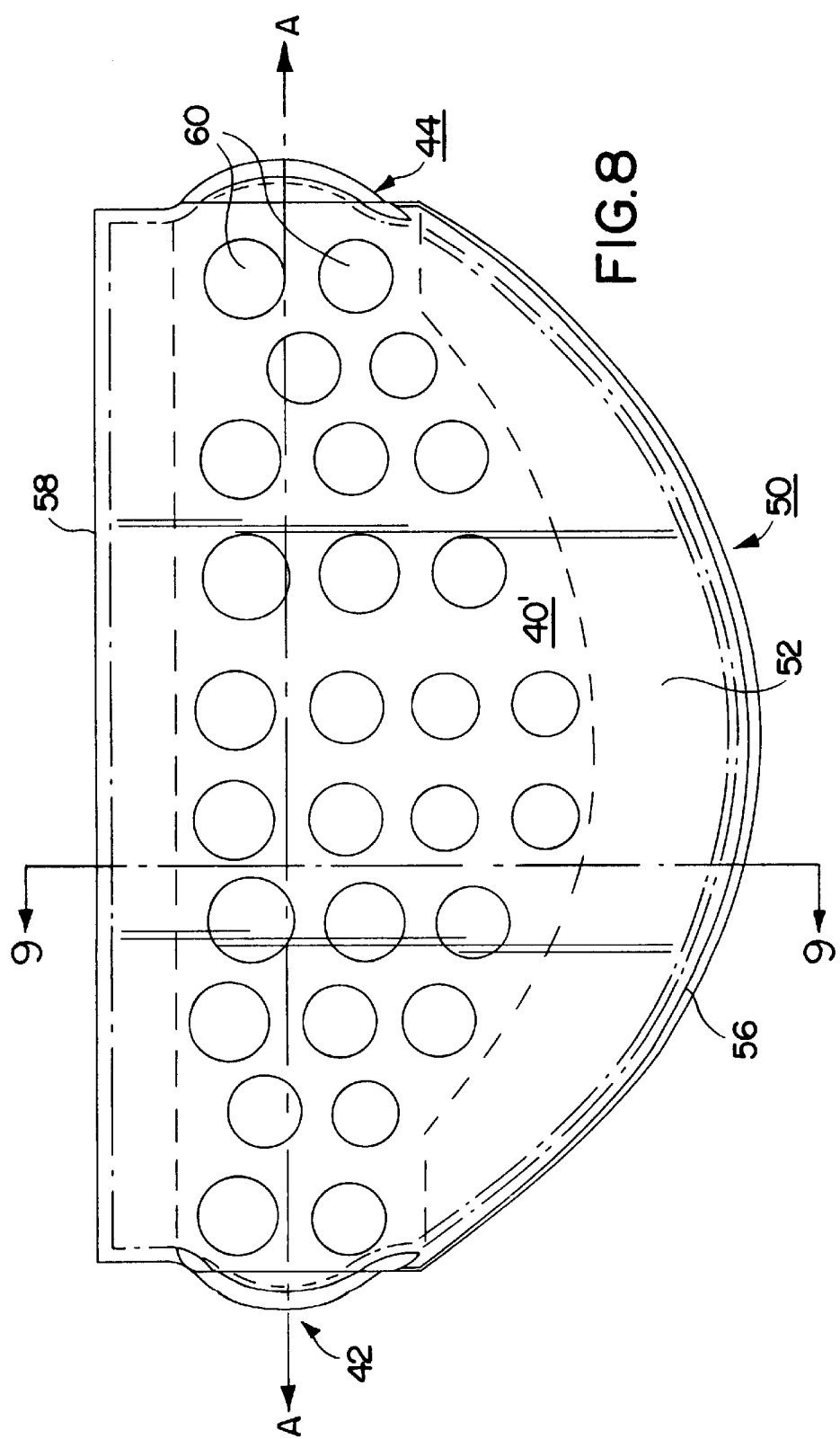

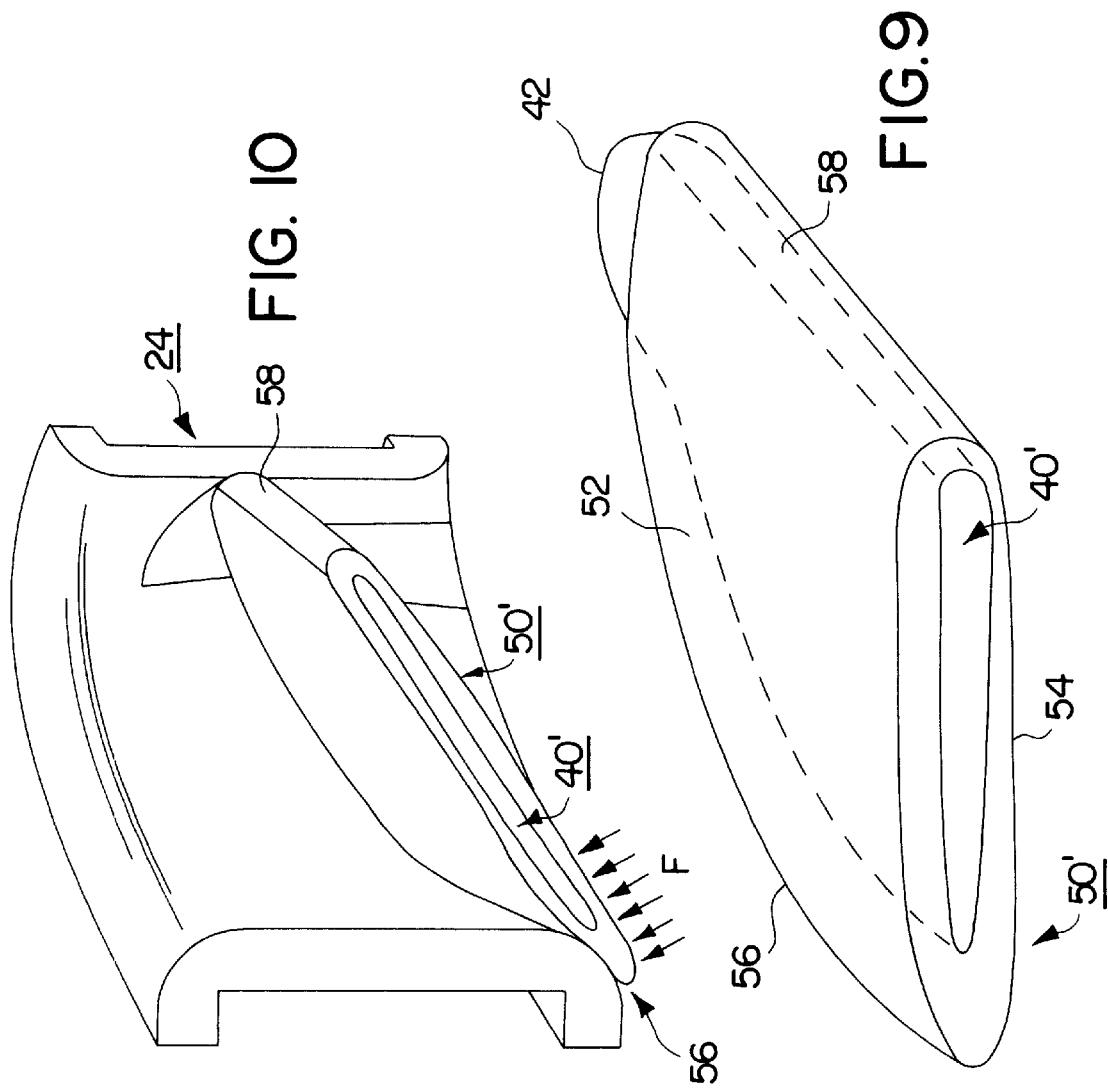

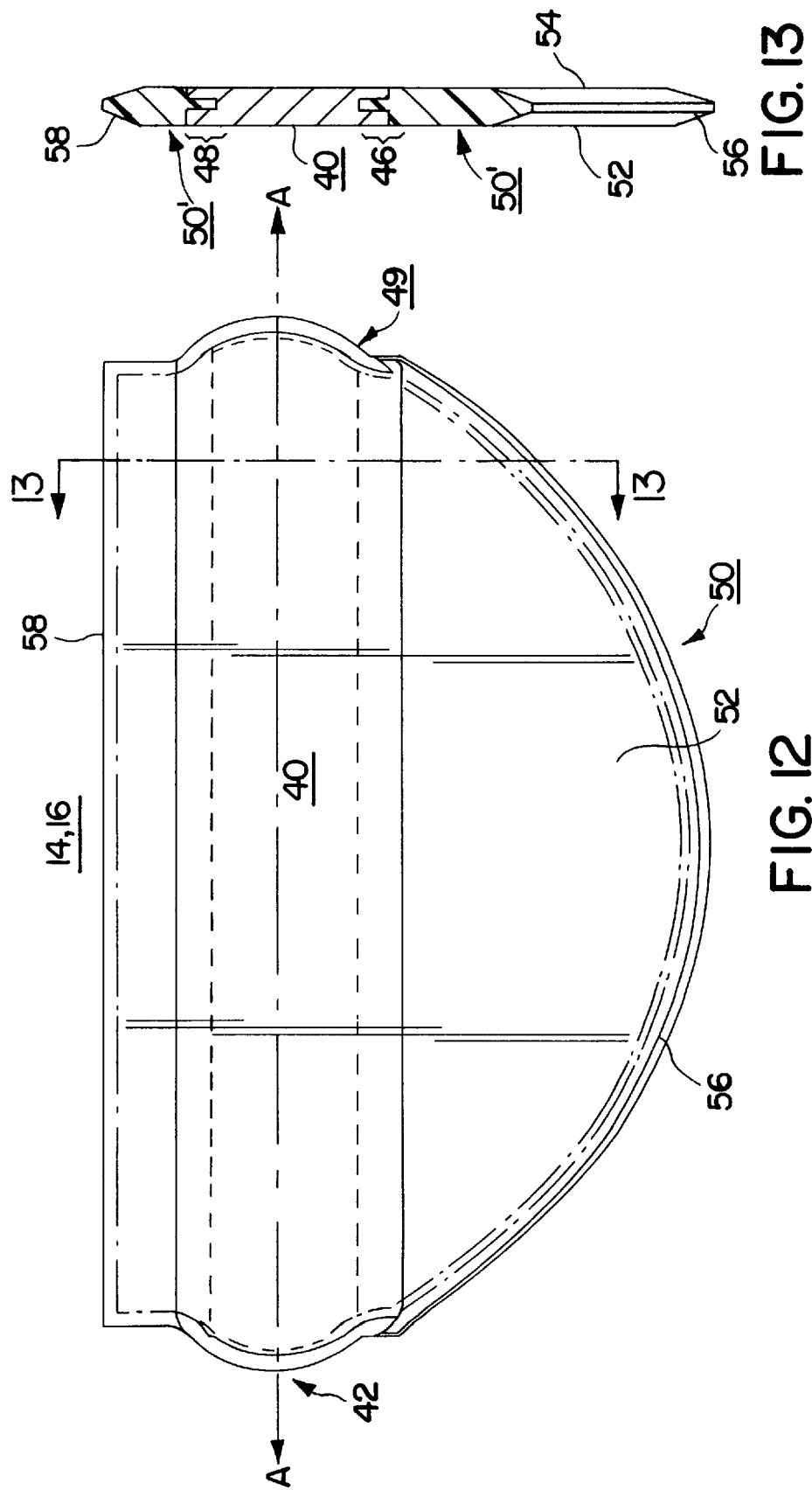

HYBRID MECHANICAL HEART VALVE PROSTHESIS

FIELD OF THE INVENTION

The present invention pertains to prosthetic mechanical heart valves and in particular, to bi-leaflet and tri-leaflet mechanical valves formed with rigid hinge mechanism and flexible leaflets.

BACKGROUND OF THE INVENTION

During each cardiac cycle, the natural heart valves alternatively open to allow blood to flow through them and then close to block blood flow. During systole, the mitral and tricuspid valves close to prevent reverse blood flow from the ventricles to the atria. At the same time, the aortic and pulmonary valves open to allow blood flow into the aorta and pulmonary arteries. Conversely, during diastole, the aortic and pulmonary valves close to prevent reverse blood flow from the aorta and pulmonary arteries into the ventricles, and the mitral and tricuspid valves open to allow blood flow into the ventricles. The cardiac valves open and close passively in response to blood pressure changes operating against the valve leaflet structure. Their valve leaflets close when forward pressure gradient reverses and urges blood flow backward and open when forward pressure gradient urges blood flow forward.

In certain individuals, the performance of a natural heart valve is compromised due to a birth defect or becomes compromised due to various disease processes. Surgical repair or replacement of the natural heart valve is considered when the natural heart valve is impaired to an extent such that normal cardiac function cannot be maintained. The natural heart valve can be replaced by homograft valves obtained from the same species (e.g., human donor heart valves), heterograft valves acquired from different species, and prosthetic mechanical heart valves.

The present invention is directed to improvements in prosthetic mechanical heart valves. Modern implantable mechanical heart valves are typically formed of a relatively rigid, generally annular valve body defining a blood flow orifice and an annular valve seat and one or more occluders that are movable between a closed, seated position in the annular valve seat and an open position at an angle to the valve body axis. These components of mechanical heart valves are made of blood compatible, non-thrombogenic materials, e.g., pyrolytic carbon and titanium. A biocompatible, fabric sewing ring is typically provided around the exterior of the valve body to provide an attachment site for suturing the valve prosthesis into a prepared valve annulus. The occluder(s) is retained and a prescribed range of motion is defined by a cooperating hinge mechanism or other restraining mechanism. Such prosthetic heart valves function essentially as check valves in which the occluder(s) responds to changes in the relative blood pressure in the forward and reverse directions as described above and move between their open and closed positions.

Two approaches to mechanical heart valve design have been followed over the years. In a first approach, the design of the mechanical heart valve structure has attempted to mimic natural heart valve structures in construction, appearance and function. For example, in U.S. Pat. No. 4,556,996, a valve design is proposed using molded elastomer, triangular flaps that extend inwardly into the annulus of a ring shaped valve body that appears to be intended to mimic tricuspid heart valves. The flaps and ring-shaped body are integrally formed of Delrin or a similar hard plastic and covered with an elastomer. The flaps are intended to bend between open and closed positions by integrally formed hinges at the junctions of the flaps and the ring shaped body.

This approach has also led to a number of proposed designs to mimic the operation of a natural tricuspid valve employing flaps formed of thin plastic membranes attached to the valve body and to struts extending downstream from the valve body leaving the flaps with free flap edges. In operation, the three flaps balloon outward in the open position to define a cylindrical annulus for blood flow. In the closed position, the free flap edges of the three flaps collapse against one another. A variety of such mechanical heart valve prostheses are described in U.S. Pat. Nos. 4,222,126, 4,364,127, 5,500,016 and 5,562,729, incorporated herein by reference.

The flexible valve leaflets of the designs following this first approach have not been successfully clinically implemented in part because the leaflet materials and integral hinge mechanisms cannot be shown to be reliable and immune from fracture or tear over long term use. It is also well known that calcium mineral deposits on the flaps causes calcification of leaflets. The calcified leaflets become rigid and fail to open and close properly. Their durability are greatly reduced and valve failure always occurs at the calcified location. Moreover, the integral hinge structures are in low blood flow regions and blood stagnation in those regions can contribute to the accretion of thrombus formation and also cause the failure of these valves.

In the second approach, less attention is paid to trying to mimic the appearance and function of natural heart valve flaps, and more attention is paid to maximizing reliability of operation and hemodynamic function. Such mechanical heart valve prostheses have employed other occluders and hinge or occluder restraint mechanisms that do not resemble flaps and integral flap hinges. A wide variety of such mechanical heart valve designs have been proposed and/or clinically used in the past. For example, U.S. Pat. No. 3,911,502 describes mechanical heart valves employing a spherical ball in a cage that moves in the cage into and out of engagement with an annular valve body seat in response to the blood flow due to normal pumping action of the heart. The spherical ball was formed of a variety of materials including metals, plastics, and silicone rubber.

Other early heart valve prostheses employed occluders in the form of a circular disc restrained within cage struts or by disk mounted struts for movement between open and closed disk positions in response to blood pressure changes, as shown, for example in U.S. Pat. Nos. 3,722,004 and 3,396,409. In the '004 patent, the disk is formed of a pyrolytic carbon or metal ring coated with silicone rubber except for the periphery 20. The periphery 20 contacts the sides of the struts to restrain movement of the disk between the disk open and disk closed positions. The silicone rubber strikes the ends of the struts to stop movement of the disk in the disk open position, and the silicone rubber coating flexes to reduce noise and shock.

Heart valve prostheses using such spherical ball or circular disk occluders provide poor hemodynamic function since the major surfaces of each such occluder remain perpendicular to the blood flow when the occluder is in the open position and therefore they impede blood flow. These types of valve designs created significant pressure drop and energy loss. Moreover, the cage and strut restraints projecting from the annular valve body can interfere with heart tissue and make implantation difficult or impossible in certain valve replacement locations. In addition, such restraint structures are difficult to manufacture with the annular valve body in a manner that assures adequate mechanical reliability over years of implantation. Fractures have been reported to have occurred at junctions that were welded together.

A wide variety of pivoting disk heart valve prostheses have been developed and clinically used wherein a single circular disk of pyrolytic carbon cooperates with strut and stop structures to pivot between a disk open position and a disk closed position. The Medtronic Hall™ mechanical heart valve employs a strut machined from the titanium block forming the annular heart valve body that is extended through a central opening in the disk to restrain its pivotal movement. Such a single pivoting disk mechanical valve design is reliable, but the opening angle of the disk in the disk open position is limited to less than 90°.

More recently, clinically used, bi-leaflet heart valve prostheses have been developed that employ a pair of semi-circular or semi-elliptical plates or leaflets that are coupled to the annular heart valve base or body through pivot hinge mechanisms that allow the leaflets to pivot on leaflet pivot axes between leaflet open and seated, closed positions. The valve body has an interior side wall defining a blood flow orifice having a central blood flow axis centrally located with respect to the interior surface. The valve body also has first and second pairs of valve body hinge elements, e.g. recesses, and first and second valve body seat regions. The pairs of valve body hinge elements provide opposed pairs of hinge pivot points and a pivot axis that extends across the valve annulus and is offset from the central axis of the valve annulus.

In such bi-leaflet valve configurations, two mirror image leaflets are typically disposed in opposed or mirror image relation to one another for alternately blocking blood flow in an inflow direction when seated in a leaflet closed position and then allowing the flow of blood through said blood flow orifice in an outflow direction when in a leaflet open position. Upon closure, each valve leaflet occludes or closes a half section of the annular valve orifice or valve annulus. Generally, each leaflet is generally semi-circular in shape and has generally opposed, inflow and outflow, leaflet major surfaces and a peripheral edge extending between the opposed leaflet major surfaces. A leaflet seat section of the peripheral edge is formed to seat against a valve body seat region when in the closed position. Each leaflet can rotate about a leaflet pivot axis extending between a pair of leaflet hinge elements, e.g., outwardly projecting leaflet ears, that cooperate with a pair of valve body hinge elements, e.g., the opposed pair of hinge recesses. The leaflets are typically planar in profile, but curved or elliptical leaflets have been proposed.

Such mechanical heart valves are typically designed in somewhat differing profile configurations for replacement of different impaired natural heart valves. However, the basic in vivo operating principle is similar regardless of configuration. Using an aortic valve as an example, when blood pressure rises in response to left ventricle contraction or systole in each cardiac cycle, the leaflets of such a valve pivot from a closed position to an open position to permit blood flow past the leaflets in an outflow direction. When the left ventricle contraction is complete, blood tends to flow in the opposite, inflow direction in diastole in response to the back pressure. The back pressure causes the aortic valve leaflets to close in order to maintain arterial pressure in the arterial system.

The most widely accepted type of bi-leaflet heart valve presently used mounts its leaflets for pivoting movement by means of a pair of rounded ears extending radially outwardly from opposed edges of the leaflets to fit within rounded hinge recesses in opposed flat surfaces of the valve body side wall. Such bi-leaflet valves are exemplified by the mitral valve depicted in U.S. Pat. No. 4,276,658 and the aortic heart valve depicted in U.S. Pat. No. 5,178,632, both incorporated herein by reference.

More particularly, the conventional leaflet ears are received within curved hinge recesses extending radially into opposed flat surfaces of thickened wall sections inside the annulus of the generally cylindrical or annular valve body. Each hinge recess is designed in at least one respect to match the shape of the leaflet ear and is bounded by sets of leaflet stop surfaces angled to define the extreme open and closed leaflet positions. In other words, where the ear is formed as a portion of a circle having a given radius, the counterpart hinge recess is formed as a semicircle having a slightly greater radius. An inverse arrangement of the ear and recess hinge mechanism is depicted in U.S. Pat. No. 5,354,330, incorporated herein by reference, whereby the leaflet ear is replaced by a leaflet recess, and the hinge recess is replaced by a complementary shaped hinge boss.

To achieve the pivoting mechanism, the mating surfaces of the ears and recesses are precisely machined so as to provide a small but definite working clearance for the ears to pivot about the necked down pivot surface and be retained within the hinge recesses. During valve assembly, the annular valve body is deformed or distended so that the leaflet ears may be inserted into the respective hinge recesses. Each manufactured heart valve is then lab tested "dry" to ensure that the leaflets are held tightly enough to be secure against falling out of their hinge recesses, but are not so tightly engaged so as to create a binding or restricted valve action.

The range of leaflet motion is typically controlled by pins or ramps or opposed side stops of the hinge recesses or by hinge bosses in the valve body. In one format described in the above-incorporated '632 patent, the hinge recess is generally spherical and bounded by open and closed stop surfaces of a stop member projecting into the recess. In the other formats depicted in the above-incorporated, '658 patent, each hinge recess has an elongated "bow-tie" or "butterfly" appearance created by the inward angulation of opposed side edges extending from inflow and outflow end edges and meeting at opposite disposed, necked down, pivot points or surfaces intermediate the end edges.

A great deal of effort has been devoted to controlling the range of movement and the acceleration of the leaflets between the open and closed positions to both control noise and decrease wear or the possibility of leaflet fracture. Bi-leaflet mechanical heart valves are known to be noisy, in the sense that patients can frequently hear the seating of the valve leaflet peripheral edges against the valve seats upon closure. It is desirable for patient comfort to provide a bi-leaflet design that minimizes the distraction of leaflet seating noise.

It is also known that blood cells are extremely fragile and delicate and can be damaged and/or destroyed when trapped in the valve seat regions during closure of the valve leaflet or in the wiping area of the valve leaflet ears and hinge recesses or between the leaflet ears and the open and closed stop surfaces. The wiping areas of the hinge recesses have the highest potential of thrombus formation and emboli entrapment which can accumulate therein, impair the movement of the valve leaflets, and result in valve failure requiring surgical intervention. To this time, no design has been successful in eradicating this problem. Consequently, patients receiving current bi-leaflet mechanical heart valves are prescribed continuous blood anticoagulation therapy to prevent thrombus formation and thromboemboli. In our commonly assigned U.S. patent application Ser. No. 08/898, 144 filed Jul. 22, 1997, and entitled MECHANICAL HEART VALVE PROSTHESIS, we present an improved hinge design that is intended to optimize washing of the hinge regions and decrease these problems of conventional hinge mechanisms of the type described above.

In operation, the valve leaflets accelerate rapidly as the leaflets move from the leaflet open position to the leaflet closed position during the closing phase in response to a change of blood pressure. It is difficult to decelerate the leaflets before the arcuate seat section of the leaflet peripheral edge strikes the corresponding arcuate seat region of the annular valve body. Since a conventional mechanical heart valve leaflet (disk) utilized rigid material, e.g., pyrolytic carbon, the momentum of the rotating rigid leaflet (disk) and its surrounding fluid creates a high impact force due to the sudden stop when the arcuate seat section of the leaflet peripheral edge contacts the corresponding arcuate seat region of the annular valve body. This high impact force damages all blood elements entrapped in the contact region of the leaflet peripheral edge because the impact force is far beyond the bearable limit of any blood element and the dimension of this contact region is two orders of magnitude larger than any blood element. Blood hemolysis in clinical observation is one of the typical results from this high impact force.

Moreover, the blood flow pressure at the inflow side of the conventional mechanical heart valve leaflet peripheral edge can drop to near vacuum pressure due to a water hammer effect upon leaflet closure. At the instant of a leaflet closure, blood volume proximal to the leaflet peripheral edge at the inflow side tends to separate from the leaflet surface due to the moving momentum of fluid column and the abruptly stopping of the rigid leaflet. This flow separation can create a very low pressure in a very short time span, usually less than one milli-second. This very low pressure in the water hammer effect has the potential to generate cavitation which, from occurring to vanished, is less than 50 micron seconds. Material corrosion, pitting and degradation of a leaflet surface caused by cavitation has been observed in clinical use in a few mechanical heart valves. Should cavitation occur, the explosion force of cavitation bubble in a very short time duration can easily damage blood elements near cavitation sites. Even if no cavitation occurs, the low pressure field at the inflow side of the leaflet peripheral edge can cause damage to blood elements by generating high surface tension on surface membranes of blood elements.

Also, after the valve is closed, localized high speed blood flow leakage has been observed on all the current mechanical heart valves. The blood flow leakage jets occur at the gaps between leaflet and valve housing due to the large transvalvular pressure gradient in the valve closing phase. The reported shear stresses of leakage jets are beyond the surface tensile stress limits of any blood element surface membranes. Therefore, these leakage jets not only reduce the efficiency of a passive mechanical heart valve, but also damage blood elements in the leakage stream.

SUMMARY OF THE INVENTION

It is therefore an object of the present invention to minimize these problems associated with existing pivoting leaflet, mechanical heart valves.

In accordance with the first feature of the present invention, a valve leaflet having at least one leaflet hinge element is provided for cooperatively engaging with a valve body hinge element to enable movement of the valve leaflet between a leaflet open position allowing blood flow through the valve body blood flow orifice and a leaflet closed position for blocking blood flow through the blood flow orifice. The valve leaflet has generally opposed, inflow and outflow, leaflet major surfaces bounded by a peripheral edge extending between the opposed leaflet major surfaces. The peripheral edge is formed at least in part to provide a leaflet seat for engaging against the valve body seat region.

The valve leaflet is formed in a hybrid manner of a relatively rigid valve leaflet skeleton or frame and a relatively flexible valve leaflet body adhered to the frame formed of an elastic, bio-compatible material. The valve body elastic material extends over and is adhered to about at least a portion of the valve leaflet frame and extends away from the valve leaflet frame to form at least a portion of the opposed leaflet major surfaces and the peripheral edge. The leaflet body material has a resilience and thickness that allows the leaflet seat to be deformed into a contact band with the valve body seat region to absorb contact shock when the leaflet moves into the leaflet closed position. The valve leaflet frame is coupled with the valve leaflet hinge element and formed of a dimensionally rigid, bio-compatible, material providing dimensional rigidity to a portion of the valve leaflet and the leaflet hinge element. The valve leaflet frame enables the cooperative engagement of the valve body hinge element with the valve leaflet hinge element and governs movement of the valve leaflet between the leaflet open and closed positions with respect to the blood flow orifice.

The leaflet frame preferably extends in a leaflet pivot axis direction and comprises first and second valve leaflet hinge elements at the opposite ends of the leaflet pivot axis. The valve body is formed with first and second valve body hinge elements for receiving the first and second valve leaflet hinge elements, respectively, for allowing pivotal movement of the valve leaflet about the leaflet pivot axis between the leaflet open and leaflet closed positions. The leaflet body further comprises a coating of the elastic, bio-compatible material extending over the leaflet frame and forming substantially all of the opposed, leaflet major surfaces.

Preferably, the invention is implemented in a bi-leaflet valve having two such leaflets that are hinged for pivotal movement between leaflet open and leaflet closed positions with respect to first and second portions of the annular blood flow orifice and first and second valve body seat regions. Preferably, each valve leaflet frame extends between a pair of leaflet hinge elements that cooperatively engage a pair of valve body hinge elements together defining a dimensionally stable pivot axis. The first and second valve leaflets have leaflet bodies extending over substantially all of the leaflet frames formed as described in the preceding paragraph to provide first and second respective leaflet occluding sections bounded by arcuate seat sections of the peripheral edges thereof that deform when seated against respective first and second valve body seat regions in the leaflet closed position. This deformation of the resilient leaflet body blocks blood flow leakage and eliminates leakage jets through the arcuate seat sections of the peripheral edges.

In such bi-leaflet mechanical heart valves, each of the first and second valve leaflets preferably further comprise first and second respective abutting sections of the peripheral edge formed to abut against one another when the first and second valve leaflets are in the leaflet closed positions. The contact of the abutting sections blocks the leakage flow of blood through any space between the first and second valve leaflets and through the blood flow orifice. The abutting section of each valve leaflet is formed by the extension of the elastic, bio-compatible material away from the leaflet frame having a resilience and thickness that provides mutual deformation of the first and second abutting sections into a contact band with one another and absorption of contact shock therebetween when the leaflets move into the leaflet closed positions. The mutual contact of the abutting sections also decreases the intensity of contact of the arcuate seat section against the respective valve body seat region.

The leaflet body is also flexible in a region of the leaflet extending inwardly of the arcuate seat section and to the leaflet frame to allow the leaflet to flex in response to blood pressure changes in the flow field. This flexibility of the leaflet allows the leaflet occluding section to effectively bend and close earlier than a rigid metal leaflet. The flexibility also decreases the closing velocity of the leaflet and diminishes the closing impact of the arcuate seat section against the respective valve body seat region. The reduced impact effect plus the deformability of the leaflet can greatly reduce or eliminate the propensity of potential cavitation at the inflow surface of the leaflet peripheral edge.

In order to promote adherence of the valve leaflet body with the valve leaflet frame, the valve leaflet frame is formed with opposed, frame major surfaces with a plurality of openings extending through the valve leaflet frame between the opposed, major frame surfaces. The leaflet body further comprises a coating of the elastic, bio-compatible material extending over the leaflet frame and through the plurality of openings and forming substantially all of the opposed, leaflet major surfaces.

The method of adhering the leaflet body to the leaflet frame preferably comprises pre-treatment of the relatively rigid leaflet frame and molding of the elastomeric material about the frame to form the leaflet body. The leaflet frame is preferably formed of pyrolytic carbon coated on a graphite substrate, even more preferably pyrolytic carbon that is treated with certain chemical solutions such as solutions based on silane or siloxane chemistries. The leaflet body is preferably molded about the treated leaflet frame from silicone rubber or other elastomers. Compounds may be added to silicone rubber before it is molded to provide radio-opacity. The polymeric surfaces of the leaflet may be modified or treated with anticoagulation and/or anti-calcification agents to prevent any potential thrombus formation and/or leaflet calcification.

The valve frame provides for the structural rigidity and support of the valve leaflet hinge elements and absorbs shocks to the valve leaflet incurred in the opening and closing phases. The valve body moderates shocks and provides for the soft closure that reduces blood damage and mechanical deterioration of the valve leaflet structure. The resulting need for anti-coagulation drug therapy may be reduced.

The hybrid valve leaflet allows the pivoting leaflet mechanical heart valve to enjoy the gentle and smooth closing behavior of a tissue valve while retaining the long life and reliability of the mechanical heart valve. Because of the large thickness and strength of this leaflet design, potential calcification and structural deterioration as seen in conventional polymeric valves are minimized or eliminated.

These principles of construction and operation can also be applied to multi-leaflet mechanical heart valve prostheses, particularly, tri-leaflet heart valves, and the resultant advantages can enjoyed in such multi-leaflet heart valves.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 3 is a plan view of a variation of the hybrid valve leaflet of FIG. 2 viewed from the inflow surface thereof;

FIG. 4 is a partial cross-section, isometric view of the hybrid valve leaflet of FIGS. 2 and 3 taken along lines 4—4 of FIGS. 2 and 3;

FIG. 5 is a partial cross-section, isometric view of the hybrid valve leaflet of FIGS. 2 and 3 seated in the leaflet closed position against a valve body seat region;

FIG. 6 is a side cross-section view taken along lines 6—6 of FIG. 1 of a pair of the hybrid valve leaflets of FIGS. 2 and 3 seated in the leaflet closed position against one another in an abutting contact band and against first and second valve body seat regions in seat contact bands;

FIG. 7 is a plan view of an exemplary planar hybrid valve leaflet in accordance with a second embodiment of the invention viewed from the inflow surface thereof;

FIG. 8 is a plan view of a variation of the hybrid valve leaflet of FIG. 7 viewed from the inflow surface thereof;

FIG. 9 is a partial cross-section, isometric view of the hybrid valve leaflet of FIGS. 7 and 8 taken along lines 9—9 of FIGS. 7 and 8;

FIG. 10 is a partial cross-section, isometric view of the hybrid valve leaflet of FIGS. 7 and 8 seated in the leaflet closed position against a valve body seat region;

FIG. 11 is a side cross-section view taken along lines 11—11 of FIG. 1 of a pair of the hybrid valve leaflets of FIGS. 7 and 8 seated in the leaflet closed position against one another in an abutting contact band and against first and second valve body seat regions in seat contact bands;

FIG. 12 is a plan view of a further variation of the hybrid valve leaflet of FIG. 2 viewed from the inflow surface thereof;

FIG. 13 is a side cross-section view taken along lines 13—13 of the valve leaflet of FIG. 12.

DETAILED DESCRIPTION OF THE PREFERRED EMBODIMENTS OF THE INVENTION

Figure 1:
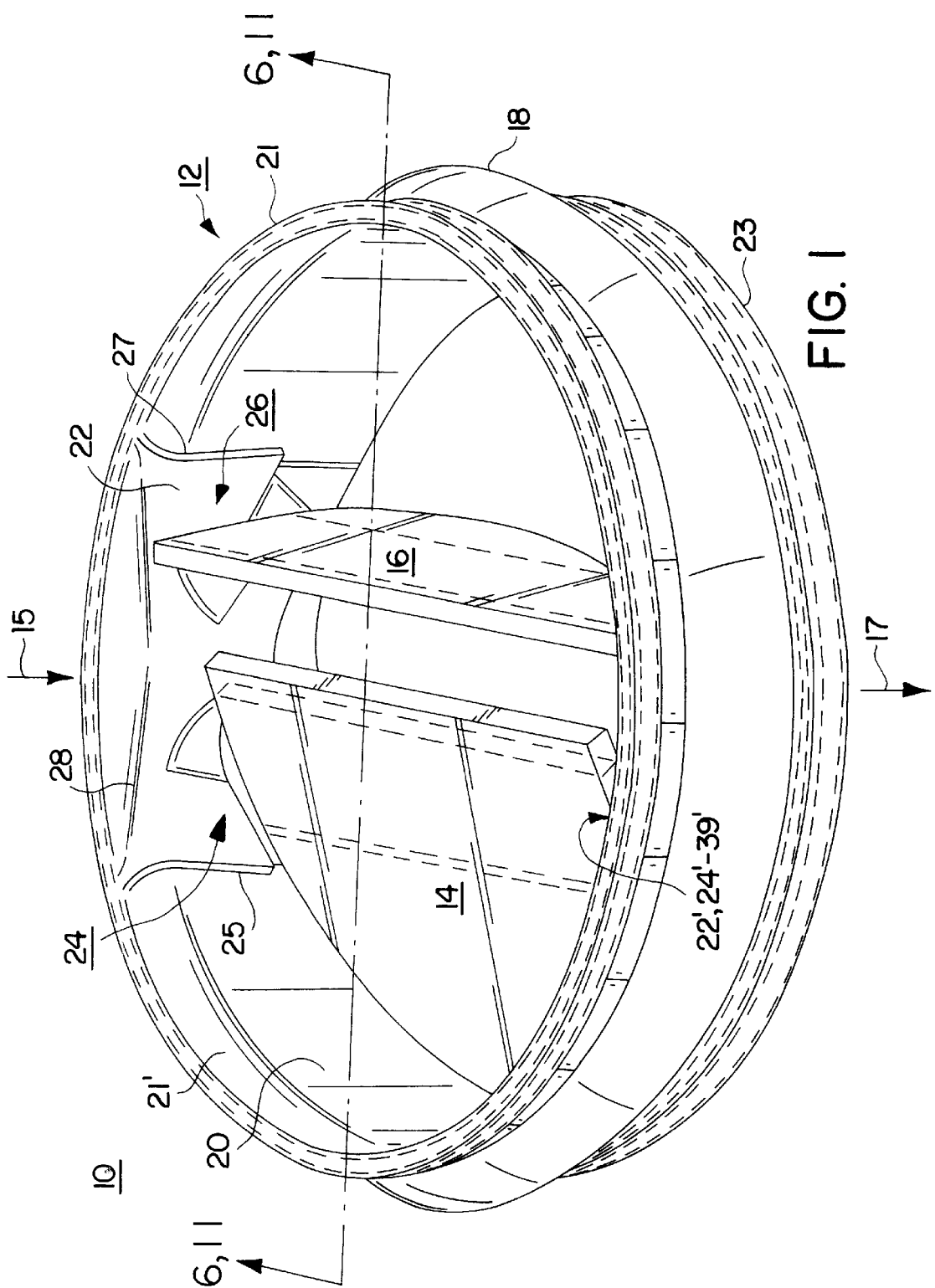
FIG. 1 is an isometric view from the inflow side of a bi-leaflet mechanical heart valve in an aortic configuration incorporating the improved hybrid leaflet of the present invention.

It will be understood that the present invention may be embodied in mechanical heart valves having occluders formed of at least one, two or conceivably three or more leaflets, wherein the leaflets are formed in a hybrid fashion from a leaflet frame and a leaflet body as summarized above and explained in detail below. FIG. 1 depicts at least one preferred form of such a bi-leaflet mechanical heart valve in an aortic valve configuration having a low, narrow profile that follows the general configuration of that disclosed in application Ser. No. 08/898,144, in which the present invention may be implemented. It will be understood that the hybrid valve leaflets can be implemented in a wide variety of pivoting disk or leaflet mechanical heart valve designs having differing hinge mechanisms. It will also be understood that the hybrid valve leaflets can be used in different valve designs that have different leaflet or disk open and closing directions.

In FIG. 1, the heart valve 10 includes four major components, that is, an annular valve body 12, an occluder comprising first and second leaflets 14 and 16, and a fabric sewing ring 18. The first and second leaflets 14 and 16 are depicted in the leaflet closed, seated position and the leaflet open position, respectively, simply to illustrate the range of motion of the leaflets between these extreme positions. When in the closed position, the generally semi-circular sections of the peripheral leaflet edges constitute leaflet seats that are seated in contact with respective valve body seat regions extending around respective halves of the annular valve body 12. The relatively straight sections of the peripheral edge extending between the opposed leaflet ears contact one another at the centerline of the valve annulus.

The fabric sewing ring 18 (shown not necessarily to scale) may take any of the forms known in the art and is preferably rotatable about an outer sewing ring channel formed in the outer wall of the annular valve body 12 between exterior flanges of the annular, inflow and outflow rims 21 and 23. The details of the construction, retention, and use of the sewing ring 18 are not important to the present invention, and may take any of the known forms. Preferably, the valve body 12 may be formed of machined and polished titanium or of pyrolytic carbon or of a graphite substrate coated with pyrolytic carbon in a manner well known in the art of mechanical heart valve fabrication. The valve leaflets 14 and 16 are preferably formed in accordance with the following description of the preferred embodiments.

The heart valve 10 has a plane of symmetry extending through its midsection defined as coincident with the central axis 11 of blood flow through the annulus or annular orifice of the valve body 12 and extending equidistantly between the parallel edges of the leaflets 14 and 16. The heart valve 10 is to be implanted so that forward blood flow is downward in FIG. 1 defining an inflow side and inflow blood direction 15 and an outflow side and outflow blood direction 17 of the heart valve 10. An increase in blood pressure on the inflow side exceeding the blood pressure on the outflow side causes both of the leaflets 14, 16 to swing open from the seated position of leaflet 14 to the open position of leaflet 16. Conversely, when the relative blood pressure reverses, the back pressure on the outflow side causes the leaflets 14, 16 to swing closed from the open position to the closed position of leaflet 14.

The valve leaflets 14, 16 are constructed in mirror image fashion, and each have generally opposed major planar inflow and outflow side surfaces and a peripheral edge extending between the opposed major surfaces. An arcuate seat section of the peripheral edge of each valve leaflet seats against a corresponding arcuate seat region of the annular interior side wall 20 of the annular valve body 12 in the closed position. Each valve leaflet 14, 16 is also formed with a pair of convexly projecting leaflet hinge elements or ears at opposed locations along the opposite ends of the arcuate seat section of the peripheral edge whereby a leaflet pivot axis A—A is defined extending between the leaflet ears. The relatively straight, abutting sections of the valve leaflets 14, 16 contact one another when the leaflets 14, 16 are in the closed position The annular valve body 12 includes a generally continuous, circular interior side wall 20 intermediate the inflow and outflow rims 21 and 23 defining a valve annulus of a predetermined diameter. The interior side wall 20 is thickened in two diametrically opposed formations and have major planar surfaces 22, 22' that are generally mirror images of one another and are preferably parallel to one another and bounded by planar surface edges. The planar surface 22 intersects the curved surface of the interior side wall 20 along planar surface side edges 25 and 27. The planar surface 22 is bounded on the inflow and outflow sides by concave, planar surface, inflow and outflow edges that extend concavely inwardly from inflow and outflow rims 21 and 23, respectively. Respective inflow and outflow chamfers are formed between the inflow edge 28 and inflow rim 21 and between the outflow edge 30 and outflow rim 23. The planar surface 22' is formed and bounded in the identical, mirror image manner as planar surface 22.

Valve body hinge elements or recesses 24, 26 and 24', 26' are formed in the planar surfaces 22, 22' such that pairs of hinge recesses 24, 24' and 26, 26' are diametrically opposed to one another across the annular orifice. Each hinge recess 24, 24', 26, 26' extends concavely outwardly from each planar surface 22, 22' and into the thickened formation of the annular body interior side wall 20. Each hinge recess 24, 24', 26, 26' is shaped in recess depth to form a pivot bearing surface for receiving a convexly projecting ear bearing edge of a valve leaflet 14, 16. Each hinge recess of the hinge recess pairs 24, 24' and 26, 26' has opposed recess side edges shaped and oriented to allow and bound movement of the respective valve leaflet 14, 16 between the open and closed positions.

A particular preferred hinge configuration of the cooperating leaflet and valve body hinge elements is described further in the Ser. No. 08/898,144 application. However, any hinge configuration may be employed in the practice of the present invention where the leaflet hinge elements are incorporated into and supported by the leaflet frame. In accordance with the preferred embodiment of the present invention, the leaflets 14, 16 are constructed in a hybrid manner with the leaflet body formed about and extending from the leaflet frame to obtain the beneficial soft closing action of valves employing flexible flaps while retaining the beneficial hinge operation.

Figure 2:
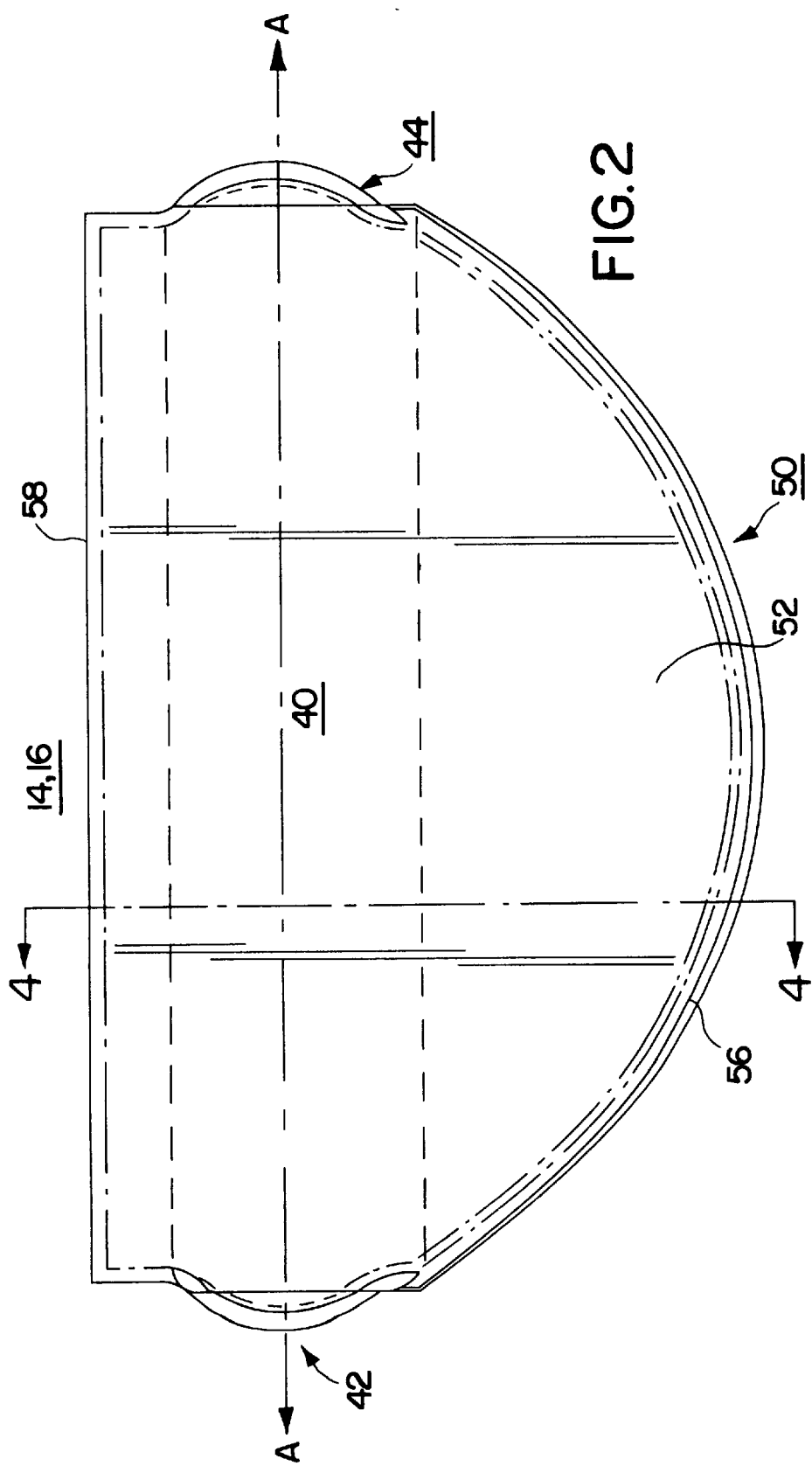
FIG. 2 is a plan view of an exemplary planar hybrid valve leaflet in accordance with a first embodiment of the invention viewed from the inflow surface thereof.

A first embodiment of the hybrid valve leaflet 14, 16 is depicted in plan view in FIGS. 2 and 3, wherein the leaflet body 50 is depicted encasing the leaflet frame 40 (shown in dotted lines). The leaflet frame 40 has generally parallel opposed major surfaces and parallel side edges and is therefore generally rectilinear. The opposite ends of the leaflet frame extend convexly outward into integrally formed leaflet hinge elements or ears 42 and 44. The leaflet ears 42 and 44 are shaped in convex profile to fit in and conform with the generally concave valve body hinge elements or recesses 24, 24' or 26, 26' formed in the planar surfaces 22, 22' of the valve body. The leaflet ears 42, 44 and the leaflet frame 40 are preferably machined out of a single piece of rectilinear stock so that the assembly is mechanically rigid and stable. The leaflet frame 40 provides the dimensionally stable, leaflet pivot axis A—A extending between the leaflet ears 42 and 44. Preferably the leaflet frame 40 and the integral leaflet ears 42, 44 are formed of a graphite substrate that is coated with pyrolytic carbon. The pyrolytic coating is polished in the region of the leaflet ears 42 and 44 and may be otherwise surface treated elsewhere to promote adhesion of the leaflet body 50 to the leaflet frame 40.

The leaflet body 50 preferably comprises an integral coating of an elastic, bio-compatible material extending over the leaflet frame 40 and forming substantially all of opposed, leaflet major surfaces 52 and 54 (also shown in FIGS. 4 and 5). In this first embodiment, a significant portion of the leaflet body 50 which functions as a leaflet occluding section to occlude a half section of the valve orifice when the leaflet is in the closed position is formed entirely of the elastic material which allows the leaflet body to flex in response to blood pressure changes. The opposed, leaflet major surfaces 52 and 54 extend away from the leaflet frame 40 to a peripheral edge extending between the opposed leaflet major surfaces 52, 54 except where the leaflet ears 42, 44 project away from the leaflet frame 40. An arcuate section of the peripheral edge that extends between one end of each ear 42, 44 provides an arcuate leaflet seat 56 for engaging in a contact band against an arcuate valve body seat region when the leaflet 14, 16 is in the leaflet closed position. The arcuate leaflet seat 56 of each leaflet 14, 16 deforms when seated against respective first and second valve body seat regions in the leaflet closed position.

In such bi-leaflet mechanical heart valves, the valve leaflets 14, 16 preferably each further comprise a flexible, relatively straight, abutting section 58 of the peripheral edge formed to abut against the flexible abutting section of the other valve leaflet when the first and second valve leaflets 14, 16 are in the leaflet closed positions. The mutual contact of each abutting section 58 of leaflets 14, 16 against the other abutting section 58 at least partially blocks the flow of blood through any space between the valve leaflets 14, 16 and through the blood flow orifice. The abutting section 58 of each valve leaflet 14, 16 is formed by the extension of the elastic, bio-compatible material of the valve body 50 away from the leaflet frame 40 and between the other ends of each of the leaflet ears 42, 44. The abutting section 58 of each leaflet 14, 16 extends generally parallel with the leaflet pivot axis A—A and has a resilience and thickness that provides mutual deformation of the abutting sections 58 into a contact band with one another and absorbs contact shock therebetween when the leaflets 14, 16 move into the leaflet closed positions. The mutual contact of the abutting sections 58 also decreases the intensity of contact of the arcuate seat section 56 against the respective valve body seat region.

FIG. 3 depicts a variation of the hybrid valve leaflet of FIG. 2, wherein a plurality of openings 60 are formed to extend through the valve leaflet frame 40. In this variation, the coating of elastic, bio-compatible material extends over the leaflet frame 40 and through the plurality of openings 60 to form substantially all of the opposed, leaflet major surfaces 52 and 54. The size, shape and number of openings 60 may be varied to provide optimum adhesion of the elastic material of the valve body 50 through the openings and to the valve frame 40 while retaining the structural integrity of the valve frame 40.

FIGS. 4 and 5 depict the leaflet of FIGS. 2 or 3 in partial cross-section perspective views alone and in conjunction with a section of the heart valve body 12, respectively. FIG. 6 depicts of a pair of the hybrid valve leaflets 14, 16 of FIGS. 2 and 3 seated in the leaflet closed position against one another in an abutting contact band 62 and against first and second valve body seat regions 64 and 66. The abutting contact band 62 constitutes the contact between the elongated, generally straight, abutting sections 58. The width of the abutting contact band 62 depends on the elastomeric material flexibility, thickness and width of each of the abutting sections 58.

The first and second seat regions 64 and 66 illustrated in FIG. 6 constitute the arcuate areas or bands of contact extending between the arcuate leaflet seat 56 of each leaflet body 50 against arcuate seat bands or regions extending along first and second sections of the interior side wall 20. Each of the arcuate seat regions 64, 66 generally extends in an arc from arc ends at the planar surface side edges 25 and 27, respectively, (adjacent each of the first and second pairs of valve body hinge recesses 24, 24' and 26, 26', respectively,) downward in the outflow direction toward the annular outflow rim 23 where the mid-point of each arcuate leaflet seat 56 contacts the interior side wall 20. The contact band width of the seat regions 64, 66 can vary from a maximum width where the mid-point of each arcuate leaflet seat 56 contacts the interior side wall 20 (as shown in the cross-section view of FIG. 6) to a simple line of contact at the side edges 25, 27 of the major planar surfaces 22, 22'. The contact band widths of the abutting seat regions 64, 66 depend on the elastomeric material flexibility, thickness along the arcuate leaflet seat 56 and the overall dimensions of the leaflet body 50.

In the example illustrated in FIG. 5, the arcuate seat region 64 extends over the convex portion of the annular outflow rim 23, whereas in the example illustrated in FIG. 6, the arcuate seat regions 64, 66 intrude less upon the convex portion of the annular outflow rim 23. The arcuate paths of the seat regions 64, 66 depend upon the thickness of the polymer material. The FIG. 6 embodiment is preferable for a thicker leaflet configuration, while the FIG. 5 embodiment is the choice for a thin leaflet configuration.

Because the major portion of the leaflet is constructed by polymeric material as shown in FIGS. 2 to 8, the leaflet body is flexible in the region of the leaflet extending toward the arcuate seat section. This flexibility allows the leaflet to flex in response to blood pressure gradient changes in the flow field surrounding the leaflet inflow and outflow surfaces during the leaflet opening phase. The reverse pressure gradient in the blood stream can cause the flexible leaflet to move towards closing earlier than the conventional rigid leaflet, mimicking the behavior of a tissue valve cusp, and minimizing back flow volume.

The preferred first embodiment employs a leaflet frame 40 that is minimized in size to that sufficient to provide a dimensionally stable leaflet pivot axis A—A, to support the leaflet ears 42, 44, and to absorb any opening and closing shock as the leaflets 14, 16 reach the leaflet open and closed positions, without risk of fracture or other failure. Opening and closing shocks occur in the typical prior art pivoting leaflet mechanical heart valves when a structure of the leaflet contacts a stop surface or structure of the valve body hinge elements, e.g., when an edge of the leaflet ear contacts an open or a closed stop bounding the side edges of the butterfly shaped recesses. Shocks are also imparted to the valve leaflet when the typical single material leaflet seats in the closed position against the valve seat region or and/in abutting contact with one another. In accordance with the present invention, these shocks are reduced by the use of the elastomeric material for the valve body and the closure illustrated in FIG. 6. The elastomeric material along the arcuate leaflet seat 56 and the abutting section 58 have a resilience and thickness that provides deformation of the leaflet seat 56 into a contact band with the valve body seat region 64, 66. The width of the band contact and the resulting deformation may start before edge contact of the leaflet ears 42, 44 with a respective closed stop of the hinge recesses and thereby absorb the contact shock when the leaflet 14, 16 moves into the leaflet closed position.

Blood hemolysis has always been a problem related to the prior mechanical heart valves. Because of the flexibility of the leaflet at the leaflet edges, the width of the contact band is over two orders of magnitudes larger compared with the dimension of blood elements. All blood elements trapped in the contact band between the arcuate seat region of the leaflet peripheral edge and the arcuate set region of the valve housing body can be damaged by the high impact force created by the current rigid mechanical heart valve leaflets. The sensitive response of the hybrid leaflet of the present invention in a pressure field can decrease the closing velocity of the leaflet and diminish the impact force of leaflets against the respective valve body arcuate seat region upon closure thereby greatly reducing hemolysis and damage to blood elements. Because the polymeric portion of the leaflet can deform at the arcuate seat region of the leaflet, the deformation of the leaflet at the closing instant can totally eliminate the "water hammer" effect which occurs at the inflow side of the leaflet peripheral edge due to flow separation. Therefore, the reduced impact effect plus the deformation of the leaflet can greatly reduce or eliminate the propensity of potential cavitation at the inflow surface of the leaflet peripheral edge.

As shown in FIGS. 5, 6, 10 and 11, the deformed polymeric portion of the leaflet under the closed static force F can eliminate gaps between the arcuate seat regions on the leaflet peripheral edge and the arcuate seat regions on the respective valve housing body. This is one of the major features of the present invention which seals the valve housing body and eliminates blood flow leakage and leakage jets along the peripheral edge. This feature not only eliminates the damage to blood elements by leakage jets at the peripheral edge, but it also increases the pumping efficiency of a heart by reducing leakage volume after a valve is closed.

The use of an elastomeric, bio-compatible material, e.g., silicon rubber or polyurethane, for the leaflet body 50 is also beneficial because such materials have been clinically used with a long clinical history and have excellent mechanical properties. The surfaces of these materials also may be modified or treated with anti-coagulation and/or anti-calcification agents to prevent any potential thrombus formation and/or leaflet calcification.

It is also possible to make the leaflet frame 40 larger in area to the point where it extends substantially to the edges of the leaflets 14, 16, so that the unsupported portion of the leaflet body 50 is relatively small in proportion to the leaflet frame. In this second embodiment, the leaflet body comprises a coating over the opposed surfaces of the leaflet frame and the abutting section 58 and the arcuate leaflet seat 56. FIGS. 7–11 depict the second embodiment and variations thereof wherein the leaflet frame 40' is larger than the leaflet frame 40 and extends toward the arcuate leaflet seat 56. The relative size of the leaflet frame 40 may vary from the relationships depicted in the figures to change the leaflet thickness. With the second embodiment, the polymeric portion of the leaflet can be thinner comparing to the first embodiment because the leaflet frame 40' of the second embodiment can provide more mechanical strength and rigidity to prevent excessive leaflet bending. The leaflet frame 40' of the second embodiment can also provide more openings to promote mechanical interlocking between the pyrolytic carbon and polymeric material.

In these illustrated embodiments, the opposed, leaflet major surfaces 52, 54 are relatively planar. The thickness of the valve bodies between the opposed, major leaflet surfaces 52, 54 may be constant or may vary by tapering the thickness in the regions of the arcuate leaflet seat 56 and the abutting section 58 toward the peripheral edge as illustrated, for example, in FIGS. 5–6 and 9–11. The thickness of the leaflet body material coatings over the major surfaces of the leaflet frame 40 in proportion to the thickness of the leaflet frame are exaggerated in these figures for ease of viewing.

In the variations to the first and second embodiments illustrated in FIGS. 2 and 8, circular holes or openings 60 are depicted. It will be understood that the openings 60 are provided to increase adherence of the leaflet body with the leaflet frame, and the size, number, shape, directions and locations of such openings 60 may be varied. for example, hexagonal or lattice shape openings or perforations of the same or differing sizes may be used to provide the through bores for adherence of the encapsulating material therethrough and to maintain structural strength and integrity of the leaflet frame 40, the leaflet body 50 and the resulting hybrid valve leaflet.

In the preferred embodiments illustrated in FIGS. 1–11, the leaflet body 50 is depicted as a single molded piece that substantially encases the valve frame and, in illustrated variations, extends through openings in the leaflet body. This approach maximizes the areas of contact with either a solid leaflet frame or a perforated leaflet frame. In a further variation, the leaflet body may be formed in two parts and not coated over the major surfaces of the leaflet frame. In these embodiments, a solid leaflet frame 40 or 40' as depicted in FIGS. 2 and 7 may be employed with a frame edge configured to receive and securely support bands of elastomeric material that extend outward from the frame leaflet major edges.

FIGS. 12 and 13 depict an example of such a construction where the leaflet body 50' is formed in two parts that are adhered in edge adhesion sections 46 and 48 to the lateral edges of the leaflet frame 40. The leaflet body 50' is formed with the arcuate leaflet seat 56 and the relatively straight abutting section 58. The edge adhesion may be accomplished at the edge adhesion sections by creating open slots on the frame 40. These open slots can provide locking mechanism between the frame 40 and the leaflet seat 56 and the abutting section 58. This attachment variation may be applied as well to he second embodiment of FIG. 7.

Figure 14:
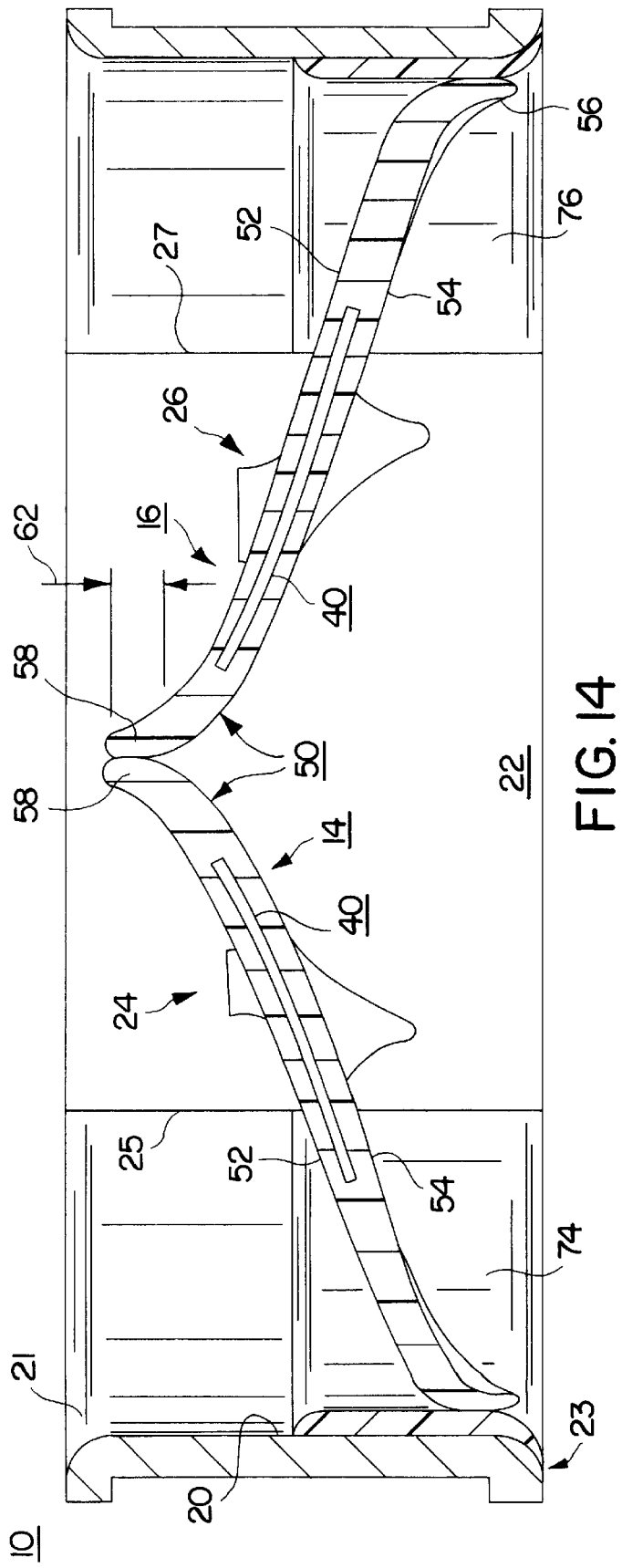
FIG. 14 is a modification of FIG. 6 depicting the use of elastomeric coatings applied to sections of the interior side wall of the valve body in the first and second valve body seat regions.

In a still further embodiment, an elastomeric coating or coatings may also be applied to at least a portion of the interior side wall 20 particularly along the first and second seat regions 64 and 66 as seat region stops or bumpers to further soften the closure of the arcuate leaflet seats 56. Two coating bands 74 and 76 are illustrated in FIG. 14 that are coated on the outflow half of the interior side wall 20 between the side edges of the major planar surfaces 22 and 22' and to the annular outflow rim 23 and cover the area of the first and second valve body seat regions 64, 66. The entire surface of the interior side wall 20 except for the major planar surfaces 22, 22' may be coated with the coating bands 74, 76. Or just substantially all of the first and second seat regions 64 and 66 may be covered by the coating bands 74 and 76. It will be understood that the depicted thickness of the coating bands 64 and 66 is highly exaggerated for ease of illustration.

It will be understood that the coating bands 74 and 76 could conceivably be employed as seat region shock absorbers or bumpers in such pivoting leaflet heart valves where the valve leaflets are formed entirely of pyrolytic carbon in the conventional manner. However, if such were undertaken, there is a high likelihood that the leaflet edges would abrade away the coating over the seat regions on closure tot he seated positions. In accordance with this aspect of the present invention, the contact between the flexible leaflet seats 56 and the coating bands 74, 76 in the seat regions 64, 66 is not as forceful partly because both are formed of the flexible elastic material and partly because the contact velocity is lowered by the flexing of the elastic material of the leaflet body 50 in the closing phase.

The method of adhering the leaflet body 50 to the leaflet frame 40 preferably comprises pre-treatment of the relatively rigid leaflet frame 40 and molding of the elastomeric material about the leaflet frame 40 to form the leaflet body 50. The leaflet frame 40 is preferably formed of pyrolytic carbon coated on a graphite substrate. The surface of frame 40 is treated with chemical coating. The leaflet body 50 is preferably molded about the treated leaflet frame 40 from silicone rubber. Compounds may be added to silicone rubber before it is molded to provide radio opacity. The polymeric surfaces of the leaflet body 50 may be modified or treated with anti-coagulation and/or anti-calcification agents to prevent any potential thrombus formation and/or leaflet calcification.

In general, the method of adhering the leaflet body 50 to the leaflet frame 40 comprises (1) depositing an oxygen-containing, silicon-containing film forming monomer on the pyrolytic carbon surface, then (2) applying an organosilane primer to the surface; and then (3) adding silicone to the primed surface. Full details of this method are disclosed in the copending U.S. patent application entitled "Plasma Process for Surface Modification of Pyrolytic Carbon," application Ser. No. 09/285,953 filed Apr. 2, 1999, which is assigned to the assignee of this application. The following is an excerpt from that application.

Figure 15:
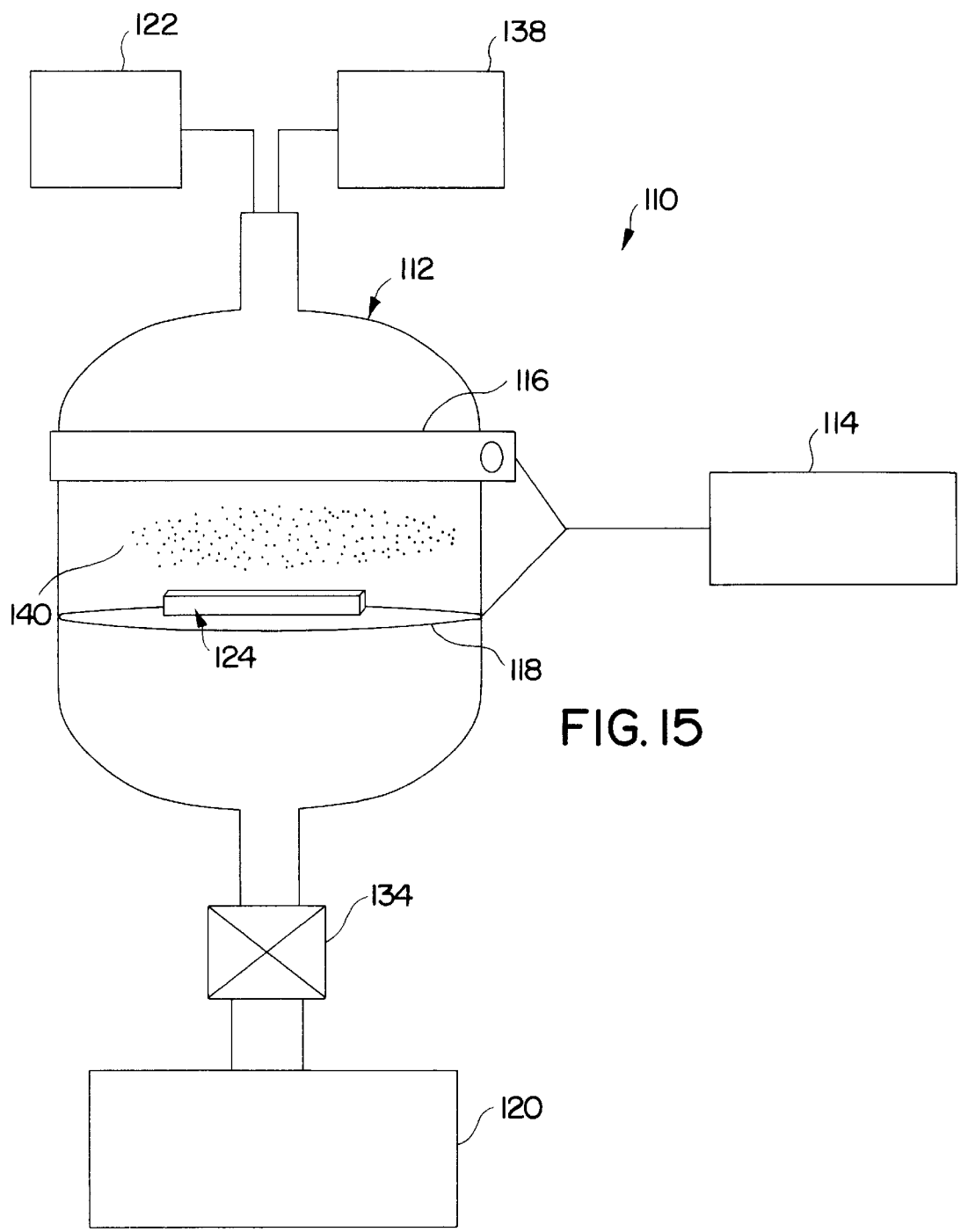
FIG. 15 is a schematic of an apparatus for use in a surface treatment method in accordance with the present invention.

FIG. 15 illustrates in schematic form a plasma reactor 110 that can be employed in a method in accordance with the present invention. The plasma reactor 110 includes, in general, a vertical reaction chamber 112, R.F. power source 114 coupled across upper and lower electrodes 116 and 118, vacuum pump 120 and a reactant monomer source 122 in fluid communication with the reaction chamber 112. Preferably, the reactant monomer source 122 also includes a means for controlling the flow rate of the monomer (not shown).

A substrate having at least one pyrolytic carbon surface 124 is disposed on one electrode, for example, the lower electrode 118. Optionally, the electrode 118 can be brought to a suitable temperature by a heating/cooling unit (not shown) that may be located in close proximity to electrode 18 and electrically controlled by a temperature control unit (not shown).

Optionally, a bellows (not shown) may be provided to adjust the spacing between the electrodes and, hence, controlling the confinement of the plasma 140. Preferably, a throttle valve 134 may be provided to control the pressure in the reaction chamber 112. The parameters that typically control the film characteristics formed from the reactant monomer include gas composition, gas flow rate, R.F. power, pressure, and temperature. Typically, the R.F. power can range from about 40 Watts to about 100 Watts, but is preferably at about 100 Watts. The pressure is typically about 0.1 Torr. Preferably, the deposition is allowed to continue from about 15 seconds to about 4 min., more preferably about 15 seconds.

Preferably, the reactant monomer is an oxygen-containing, silicon-containing film forming monomer. More preferably, the reactant monomer is a siloxane compound having the general formula $(Si-O-Si)_z R'_{3x}$, wherein z is 1 or more and x is 1 or more, and even more preferably, z is 1 and x is 1. Suitable reactant monomers include hexamethyldisiloxane (HMDS), polydimethylsiloxane, cyclic dimethylsiloxane, and the like. Typically, the reactant monomer is supplied at a gas flow of about 10.0 sccm.

Even more preferably, the reactant monomer is introduced into the reaction chamber with an inert gas from source 138 that may be in fluid communication with the reaction chamber 112. An inert gas can be selected from the group of argon, helium, nitrogen, neon, and the like. Combinations of the inert gases can also be beneficial to make the initiation of discharge easier. For example, argon can be added to neon in a minor amount to improve plasma initiation. Preferably, the monomer is provided in the reaction chamber in a ratio with the inert gas of about 20 parts monomer to about 1 part inert gas. For example, the monomer gas flow rate is more preferably about 10.0 sccm and the inert gas flow rate is more preferably typically about 0.5 sccm. Of course, one skilled in the art will readily appreciate that the deposition rate of the reactant monomer depends on the gas composition and is directly proportional to the gas flow rate, power, pressure, and is inversely proportional to temperature so that one could empirically determine the optimum parameters, such as those indicated above, for desired film characteristics.

Preferably, prior to plasma depositing an oxygen-containing, silicon-containing monomer on the pyrolytic carbon surface, it is thoroughly cleaned to remove any contaminating debris and the like. Conventional techniques can be used to adequately clean the surface, such as ultrasonic cleaning in an aqueous solution, solvent cleaning, and the like.

Once a pyrolytic carbon surface has been plasma modified as described above, a polymer can now be applied to the surface. In one embodiment of the present invention, a polymer useful in modifying the physical characteristics can now be applied by conventional methods.

Preferably, prior to applying a polymer to the plasma modified surface, the surface is primed in with a silane compound, preferably an organosilane compound, using conventional techniques. For example, the silane coupling agent can be dissolved at a 0% concentration in alcohol. One to three molar equivalents of water can be added to the silane/alcohol mixture and allowed to equilibrate. Optionally, this aqueous mixture can be diluted to a 10% concentration silane with a higher boiling point solvent. This silane composition can be applied to a surface by dipping, spraying, or other application techniques. The surfaces are then allowed to stand at ambient temperature for about 24 hours or can be placed at 110–120° C. for about 5–10 minutes.

Preferably, the silane coupling agent has the nonhydrolyzed formula $R_n SiM_{4-n}$, wherein n is preferably greater than 1. Preferably, M is selected from the group consisting of a halogen, a alkoxy group, an acyloxy group, or an amine group. R is preferably a hydrocarbon group that is classified as an aliphatic group, cyclic group, or a combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group, including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon—carbon double bonds, such as a vinyl group. The term "alkynyl group" means an unsaturated linear or branched hydrocarbon group with one or more triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

The term "group" is used to describe a chemical substituent that includes the unsubstituted group and the group with nonperoxidic O, N, or S atoms, for example, in the chain as well as carbonyl groups or other conventional substitution. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxylalkyls, hydroxylalkyls, sulfoalkyls, etc.

Suitable silane compounds include allyl trimethoxy silane, vinyl trimethoxy silane. These compounds can be simply brushed on the surface and dried.

Once primed, a polymer can now be adhered to the modified pyrolytic carbon surface. Polymers particularly suitable for adhering to the modified surface include a natural hydrogel, a synthetic hydrogel, teflon, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof. Additionally, a bio-active compound can be adhered to the modified surface. The bio-active compound can be applied directly to the plasma treated surface, the primed-plasma treated surface, or the primed-plasma treated surface including the polymer adhered thereto. A suitable bio-active compound can be selected from the group consisting of an antithrombotic agent, an antiplatelet agent, an antimitotic agent, an antioxidant, an antimetabolite agent, an anti-inflammatory agent, and a combination thereof. For example, one preferred bio-active compound is heparin. The subsequent addition of a polymer and/or a bio-active compound can be accomplished utilizing conventional techniques known in the art, The preferred embodiment of the present invention is described as having relatively planar valve leaflets, and it will be understood that the principles of the present invention may be implemented in mechanical heart valves that are not planar e.g., using curved leaflets. Moreover, while the preferred embodiment of the present invention is implemented in a hinge mechanism employing generally convex leaflet ears and concave hinge recesses, it will be understood that the principles of the present invention may be implemented into a valve hinge mechanism that is configured in an inverse relationship of the leaflet ear and hinge recesses. The present invention may also be implemented in single pivoting leaflet, heart valve designs or in heart valve designs employing more than two leaflets. The pivoting hinge mechanism in each case is supported by a frame that defines a stable mechanical leaflet pivot axis, and the flexible leaflet body functions to soften at least the closing shock of the leaflet.

Obviously, many modifications, and variations of the present invention are possible in light of the above teachings. For example, the assembly methods illustrated herein may be adapted to valves having a number of leaflets different from two or to leaflets of different configuration. The opening and closing angles of the leaflets relative to the flow axis are easily determinable by one of ordinary skill in the art.

Sizing of the valve assembly and its various components, as well as tolerances therein, to provide adequate one-way valve operation—with a limited retrograde or reverse blood flow to provide a constant washing action and motion— are easily determinable by a person of ordinary skill in the art. The present invention may be implemented in mitral and aortic valve configurations.

The present invention is particularly useful in a prosthetic heart valve where the valve body and the valve leaflet frame, and the hinge mechanism, is coated in its entirety with pyrolytic carbon. The physical characteristics of pyrolytic carbon from the standpoint of strength and wear result in a highly desirable valve. Furthermore, pyrolytic carbon has been found to be highly compatible with blood and is relatively non-thrombogenic. However, other materials may be employed in the practice of he invention. Moreover, we have found that the elastomeric material of the valve leaflet body is preferably selected from medical grade silicone rubber or polyurethane or the like as indicated above, although other elastic materials may prove useful in the practice of the invention.

It is therefore to be understood, that within the scope of the appended claims, the invention may be practiced otherwise than as specifically described without actually departing from the spirit and scope of the present invention.

We claim:

1. A mechanical heart valve prosthesis of the type comprising:

a valve body having an interior side wall defining a blood flow orifice having a central blood flow axis centrally located with respect to the interior surface, the valve body further comprising at least one valve body hinge element and a valve body seat region; and a valve leaflet having at least one leaflet hinge element for cooperatively engaging with said valve body hinge element to enable movement of said valve leaflet between a leaflet open position allowing blood flow through said blood flow orifice and a leaflet closed position for blocking blood flow through said blood flow orifice, said valve leaflet having generally opposed, inflow and outflow, leaflet major surfaces bounded by a peripheral edge extending between the opposed leaflet major surfaces, said peripheral edge formed at least in part to provide a leaflet seat for engaging against said valve body seat region;

said valve leaflet further comprising:

a valve leaflet frame coupled with said valve leaflet hinge element and formed of a dimensionally rigid, bio-compatible, material providing dimensional rigidity to a portion of said valve leaflet and said leaflet hinge element to enable the cooperative engagement of said valve body hinge element with said valve leaflet hinge element and govern movement of said valve leaflet between said leaflet open and closed positions with respect to said blood flow orifice; and a leaflet body of an elastic, bio-compatible material extending away from said valve leaflet frame and forming at least a portion of said opposed leaflet major surfaces and said leaflet seat, said leaflet seat having a resilience and thickness that provides deformation of said leaflet seat into a contact band with said valve body seat region and absorbs contact shock when said leaflet moves into said leaflet closed position.

2. The heart valve prosthesis of claim 1, wherein said leaflet body further comprises a coating of said elastic, bio-compatible material extending over said leaflet frame and forming substantially all of said opposed, leaflet major surfaces.

3. The heart valve prosthesis of claim 1, wherein:
said valve leaflet frame is formed with opposed, frame major surfaces and a plurality of openings extending through said valve leaflet frame; and
said leaflet body further comprises a coating of said elastic, bio-compatible material extending over said leaflet frame and through said plurality of openings and forming substantially all of said opposed, leaflet major surfaces.

4. The heart valve prosthesis of claim 1, wherein:
said leaflet frame extends in a leaflet pivot axis direction and comprises first and second valve leaflet hinge elements at the opposite ends of said leaflet pivot axis; and
said valve body is formed with first and second valve body hinge elements for receiving said first and second valve leaflet hinge elements, respectively, for allowing pivotal movement of said valve leaflet about said leaflet pivot axis between said leaflet open and leaflet closed positions.

5. The heart valve prosthesis of claim 4, wherein said leaflet body further comprises a coating of said elastic, bio-compatible material extending over said leaflet frame and forming substantially all of said opposed, leaflet major surfaces.

6. The heart valve prosthesis of claim 4, wherein:
said valve leaflet frame is formed with opposed, frame major surfaces and a plurality of openings extending through said valve leaflet frame; and
said leaflet body further comprises a coating of said elastic, bio-compatible material extending over said leaflet frame and through said plurality of openings and forming substantially all of said opposed, leaflet major surfaces.

7. The heart valve prosthesis of any of the claims 1–6, wherein a further layer of elastic, bio-compatible material is formed over said seat region of said valve body for contact by said leaflet body seat in said closed position of said valve leaflet.

8. A mechanical heart valve prosthesis of the type comprising:
a valve body having an interior side wall defining a blood flow orifice having a central blood flow axis centrally located with respect to the interior surface, the valve body further comprising first and second pairs of valve body hinge elements and first and second valve body seat regions; and
first and second valve leaflets for alternately blocking blood flow in an inflow direction when seated against the interior side wall in a leaflet closed position and then allowing the flow of blood through said blood flow orifice in an outflow direction when in a leaflet open position, each valve leaflet having generally opposed, inflow and outflow, leaflet major surfaces, a peripheral edge extending between the opposed leaflet major surfaces having a leaflet seat section of said peripheral edge formed to seat against a respective first or second valve body seat region when in the closed position and a pair of leaflet hinge elements for engaging with one of said pairs of valve body hinge elements, whereby the cooperative engagement of said valve body hinge elements with said valve leaflet hinge elements governs movement of each of said first and second valve leaflets between said leaflet open and closed positions with respect to said blood flow orifice, characterized in that each of said first and second valve leaflet further comprises:
a valve leaflet frame coupled with said valve leaflet hinge element and formed of a dimensionally rigid, bio-compatible, material providing dimensional rigidity to a portion of said valve leaflet and said leaflet hinge elements to enable the cooperative engagement of said valve body hinge element with said valve leaflet hinge element and govern movement of said valve leaflet between said leaflet open and closed positions with respect to said blood flow orifice; and
a leaflet body of an elastic, bio-compatible material extending away from said valve leaflet frame and forming said leaflet seat section and at least a portion of said opposed leaflet major surfaces, said leaflet seat section having a resilience and thickness that provides deformation of said leaflet seat section into a contact band with said valve body seat region and absorbs contact shock when said leaflet moves into said leaflet closed position.

9. The heart valve prosthesis of claim 8, wherein said leaflet body further comprises a coating of said elastic, bio-compatible material extending over said valve leaflet frame and forming substantially all of said opposed, leaflet major surfaces.

10. The heart valve prosthesis of claim 8, wherein:
said valve leaflet frame is formed with opposed, frame major surfaces and a plurality of openings extending through said valve leaflet frame; and
said valve leaflet body further comprises a coating of said elastic, bio-compatible material extending from over said valve leaflet frame and through said plurality of openings and forming substantially all of said opposed, leaflet major surfaces.

11. The heart valve prosthesis of claim 8, wherein:
said leaflet frame of each of said first and second valve leaflets extends in a leaflet pivot axis direction and comprises first and second valve leaflet hinge elements at the opposite ends of the leaflet pivot axis;
first and second valve body hinge elements are formed at opposed locations of said valve body for receiving said first and second valve leaflet hinge elements, respectively, of said first valve leaflet for allowing pivotal movement of said first valve leaflet about said leaflet pivot axis between said open and closed positions; and
third and fourth valve body hinge elements are formed at opposed locations of said valve body for receiving said first and second valve leaflet hinge elements, respectively, of said second valve leaflet for allowing pivotal movement of said second valve leaflet about said leaflet pivot axis between said open and closed positions.

12. The heart valve prosthesis of claim 11, wherein each of said first and second valve leaflets further comprises a coating of said elastic, bio-compatible material extending from said leaflet frame shock absorber over said valve leaflet frame and forming said opposed, leaflet major surfaces.

13. The heart valve prosthesis of claim 11, wherein:

said valve leaflet frame is formed with opposed, frame major surfaces and a plurality of openings extending through said valve leaflet frame; and said valve leaflet further comprises:
  a coating of said elastic, bio-compatible material extending from said leaflet frame shock absorber over said valve leaflet frame and through said plurality of openings and forming said opposed, leaflet major surfaces.

14. The heart valve prosthesis of any of the claims 8–13, wherein a further layer of elastic, bio-compatible material is formed over said seat region of said valve body for contact by said leaflet frame shock absorber in said closed position of said valve leaflet.

15. The heart valve prosthesis of any of the claims 8–13, wherein each of said first and second valve leaflets further comprises:

an abutting section of said peripheral edge formed to abut against a like abutting section of the other of said first and second valve leaflets when said first and second valve leaflets are in the leaflet closed positions to at least partially block the flow of blood through any space between the first and second valve leaflets and through the blood flow orifice.

16. The heart valve prosthesis of any of the claims 8–13, wherein each of said first and second valve leaflets further comprises:

an abutting section of said peripheral edge formed to abut against a like abutting section of the other of said first and second valve leaflets when said first and second valve leaflets are in the leaflet closed positions to at least partially block the flow of blood through any space between the first and second valve leaflets and through the blood flow orifice, said abutting section of each valve leaflet formed by the extension of said elastic, bio-compatible material away from said leaflet frame having a resilience and thickness that provides mutual deformation of said abutting sections into a contact band with one another and absorption of contact shock when said leaflets move into said leaflet closed positions.

17. A mechanical heart valve prosthesis of the type comprising:

a valve body having an interior side wall defining a blood flow orifice having a central blood flow axis centrally located with respect to the interior side wall and having first and second seat regions;

first and second valve leaflets mounted with said valve body to pivot about first and second respective leaflet pivot axes between leaflet closed positions for blocking blood flow through respective first and second portions of said blood flow orifice and leaflet open positions for allowing the flow of blood through said respective first and second portions of said blood flow orifice;

said first valve leaflet further comprising generally opposed, inflow and outflow, leaflet major surfaces bounded by a common peripheral edge extending between the opposed leaflet major surfaces, said peripheral edge formed with an arcuate first seat section formed to seat against said first seat region when said first valve leaflet is in the closed position and a relatively straight, first abutting section formed to extend across said blood flow orifice;

said second valve leaflet further comprising generally opposed, inflow and outflow, leaflet major surfaces bounded by a common peripheral edge extending between the opposed leaflet major surfaces, said peripheral edge formed with an arcuate second seat section formed to seat against said second seat region when said second valve leaflet is in the closed position and a relatively straight, second abutting section formed to extend across said blood flow orifice;

a first hinge mechanism including first leaflet hinge elements for retaining and guiding pivotal movement of said first valve leaflet about said first valve leaflet pivot axis between the first leaflet open position allowing blood flow through said first portion of said blood flow orifice and the first leaflet closed position blocking blood flow through said first portion when said arcuate first seat section is seated against said first seat region and said first abutting section extends across said blood flow orifice;

a second hinge mechanism including second hinge elements for retaining and guiding pivotal movement of said second valve leaflet about said second valve leaflet pivot axis between the second leaflet open position allowing blood flow through said second portion of said blood flow orifice and the second leaflet closed position blocking blood flow through said second portion when said arcuate second seat section is seated against said second seat region and said second abutting section extends across said blood flow orifice and abuts said first abutting section;

and wherein said first valve leaflet further comprises:
  a first valve leaflet frame composed of a dimensionally rigid and bio-compatible material that is shaped to extend along said first valve leaflet pivot axis between and supporting said first valve leaflet hinge elements; and
  a first valve leaflet body formed of an elastic, bio-compatible material adhered to said first valve leaflet frame to form said inflow and outflow, leaflet major surfaces and to form said first seat section of the peripheral edge having a material thickness and resilience allowing said first seat section to deform upon contact against said first seat region when said first valve leaflet pivots from said leaflet open position to said leaflet closed position; and said second valve leaflet further comprises:
  a second valve leaflet frame composed of a dimensionally rigid and bio-compatible material and shaped to extend along said second valve leaflet pivot axis between and supporting said second valve leaflet hinge elements; and
  a second valve leaflet body formed of an elastic, bio-compatible material adhered to said second valve leaflet frame to form said inflow and outflow, leaflet major surfaces and to form said second seat section of the peripheral edge having a material thickness and resilience allowing said second seat section to deform upon contact against said second seat region when said second valve leaflet pivots from said leaflet open position to said leaflet closed position.

18. The heart valve prosthesis of claim 17, wherein said first and second valve leaflet bodies each further comprises a coating of said elastic, bio-compatible material extending over said first and second leaflet frames to form said opposed, leaflet major surfaces and to form said respective first and second abutting sections of said peripheral edges that abut against one another when said first and second valve leaflets are in the closed position.

19. The heart valve prosthesis of claim 17, wherein said first and second valve leaflet bodies each further comprises a coating of said elastic, bio-compatible material extending over said first and second leaflet frames to form said opposed, leaflet major surfaces and to form said respective first and second abutting sections of said peripheral edges that abut against one another and are deformed to form a seal when said first and second valve leaflets are in the closed position sufficiently to at least partially block the flow of blood in the forward direction through the space between the first and second valve leaflets and through the blood flow orifice.

20. The heart valve prosthesis of claim 17, wherein:
    said first and second valve leaflet frames are formed with opposed, frame major surfaces and a plurality of openings extending through said valve leaflet frame; and
    said first and second valve leaflet bodies further each comprise a coating of said elastic, bio-compatible material extending from said leaflet frame shock absorber over said valve leaflet frame and through said plurality of openings and forming said opposed, leaflet major surfaces.

21. The heart valve prosthesis of claim 20, wherein said first and second valve leaflet bodies each further comprises a coating of said elastic, bio-compatible material extending over said first and second leaflet frames to form said opposed, leaflet major surfaces and to form said respective first and second abutting sections of said peripheral edges that abut against one another when said first and second valve leaflets are in the closed position.

22. The heart valve prosthesis of any of the claims 17–21, wherein a further layer of elastic, bio-compatible material is formed over said first and second seat regions of said valve body for contact by said leaflet frame shock absorber in said closed position of said valve leaflet.

23. The heart valve prosthesis of any of the claims 17–21, wherein each of said first and second valve leaflets further comprises:
    an abutting section of said peripheral edge formed to abut against a like abutting section of the other of said first and second valve leaflets when said first and second valve leaflets are in the closed leaflet position and
    a further leaflet frame shock absorber of an elastic, bio-compatible material extending along the abutting section of said peripheral edge that absorbs contact shock of said first and second valve leaflets against one another when said first and second valve leaflets pivot from said leaflet open position to said leaflet closed position.

* * * * *